United States Patent [19]
D'Alessio et al.

[11] Patent Number: 5,984,899
[45] Date of Patent: *Nov. 16, 1999

[54] NEEDLE PROTECTOR DEVICE HAVING A LOCKABLE PROTECTIVE COVER WHICH IS UNLOCKABLE DURING ACTUATION

[75] Inventors: Larry M. D'Alessio, Manasquan, N.J.; John F. Romano, Washington Crossing; William P. McVay, Doylestown, both of Pa.

[73] Assignee: Beech Medical Products, Inc., Largo, Fla.

[ * ] Notice: This patent is subject to a terminal disclaimer.

[21] Appl. No.: 08/920,225

[22] Filed: Aug. 25, 1997

Related U.S. Application Data

[63] Continuation-in-part of application No. 08/850,338, May 2, 1997, Pat. No. 5,795,336, which is a continuation-in-part of application No. 08/387,676, Feb. 13, 1995, abandoned, which is a continuation-in-part of application No. 08/159,053, Nov. 29, 1993, Pat. No. 5,389,085, which is a continuation-in-part of application No. 08/016,285, Feb. 11, 1993, Pat. No. 5,292,314.

[51] Int. Cl.$^6$ ..................................................... A61M 5/32
[52] U.S. Cl. ........................................... 604/198; 604/192
[58] Field of Search .................................... 604/198, 192, 604/193, 194, 195, 196, 197; 128/207.29

[56] References Cited

U.S. PATENT DOCUMENTS

| 5,295,975 | 3/1994 | Lockwood, Jr. | 604/198 |
| 5,389,085 | 2/1995 | D'Alessio | 604/198 |

*Primary Examiner*—John G. Weiss
*Assistant Examiner*—Charles W. Anderson
*Attorney, Agent, or Firm*—Daly, Crowley & Mofford, LLP

[57] ABSTRACT

A needle protector device includes a mount, to which a needle subassembly is fixed, and a protective cover for the needle telescopically coupled to the mount against the biassing of a compression spring. The protective cover is coupled to the mount by a pair of protruding lugs which engage a pair of channels in the mount. The channels each include an entrance portion adjacent the lower end of the mount and an elongated portion extending at an angle toward the upper end of the mount. When the lug is in the entrance portion, the cover is in a locked needle protection position in which the needle tip is covered. To operate the device, the device is placed against a needle-receiving surface and the mount is simultaneously pushed toward the surface and rotated with respect to the cover, causing the lug to move out of the entrance portion to unlock the cover and travel along the elongated portion of the channel. Upon removal of the needle, the compression spring biases to move the cover back over the needle.

25 Claims, 14 Drawing Sheets

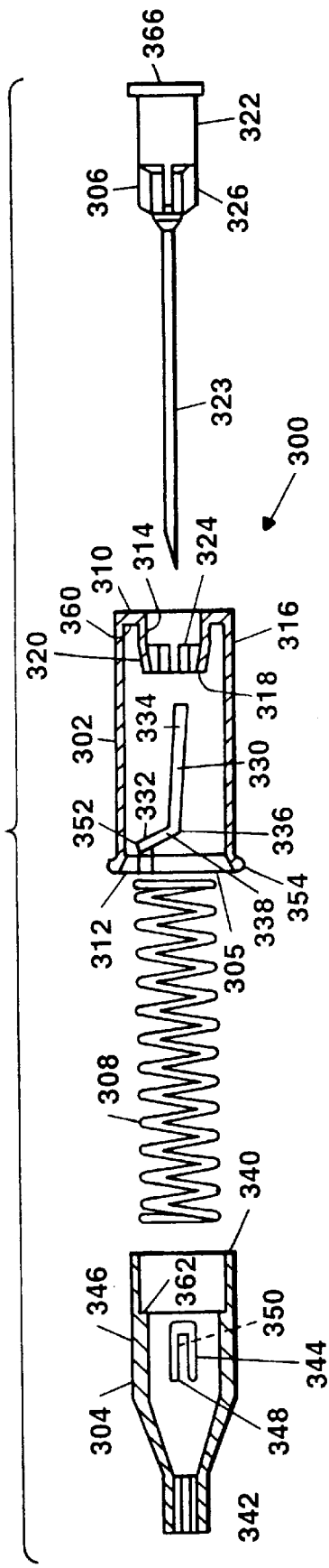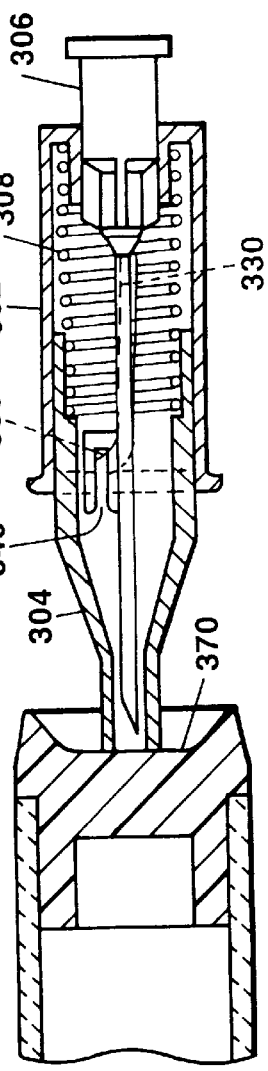
Figure 25
Figure 26

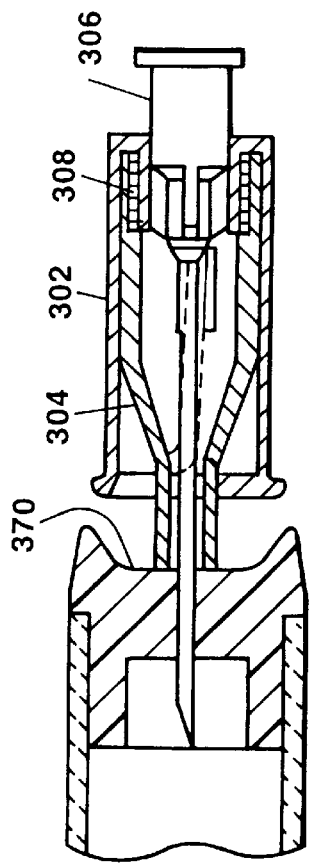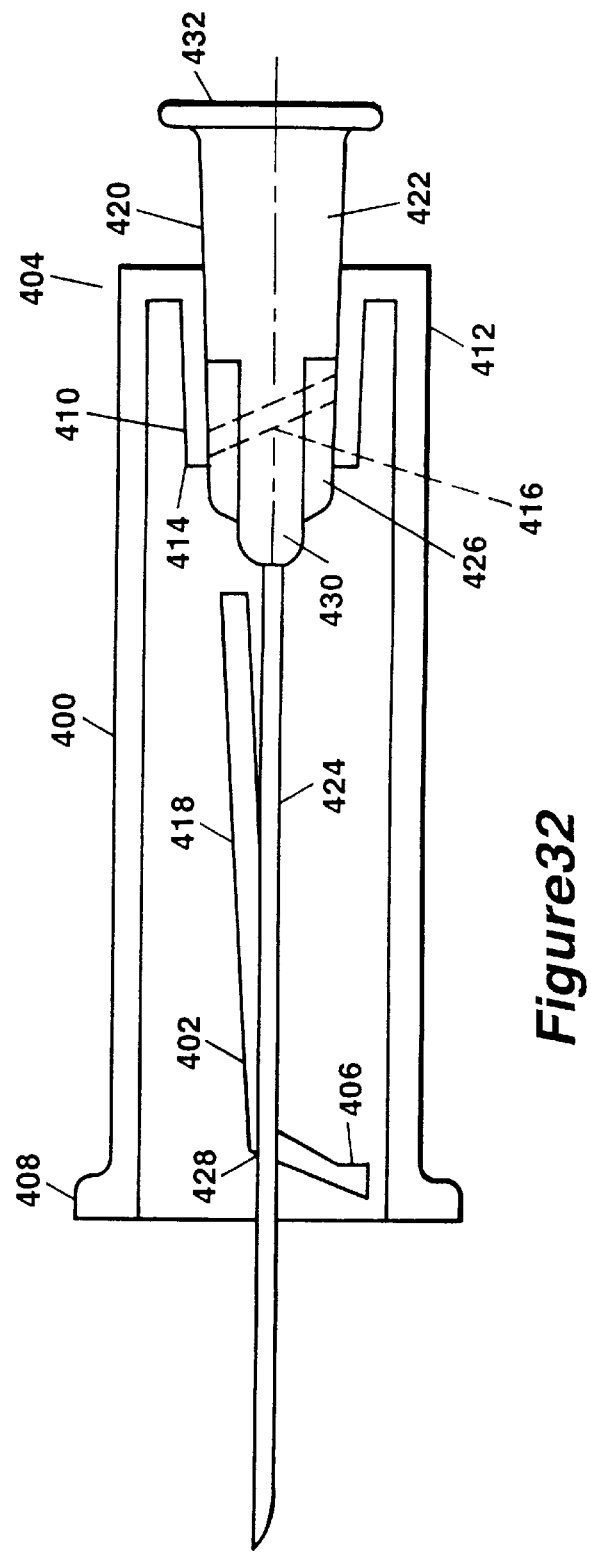

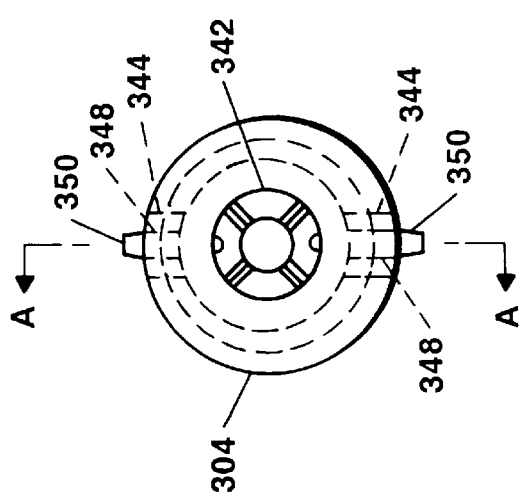
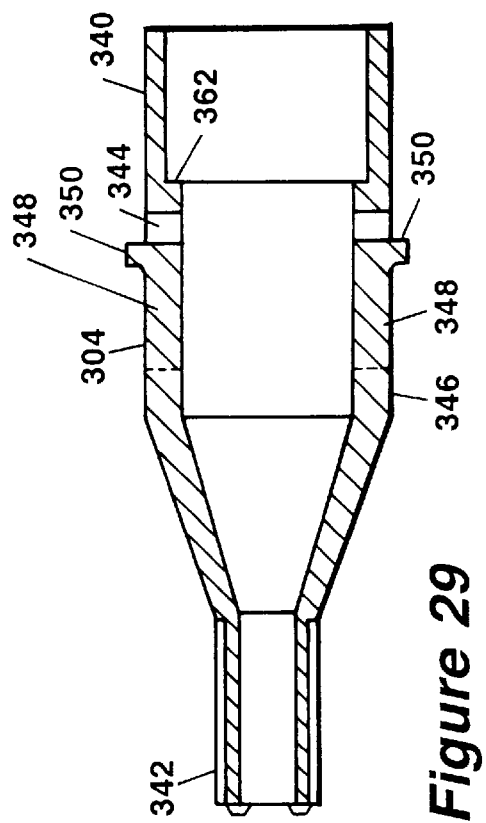

NEEDLE PROTECTOR DEVICE HAVING A LOCKABLE PROTECTIVE COVER WHICH IS UNLOCKABLE DURING ACTUATION

CROSS-REFERENCE TO RELATED CASE INFORMATION

This application is a continuation-in-part of File Wrapper Continuation application Ser. No. 08/850,338, now U.S. Pat. No. 5,795,336 filed on May 2, 1997, entitled AUTOMATIC NEEDLE PROTECTOR HAVING FEATURES FOR FACILITATING ASSEMBLY, which is a continuation-in-part of U.S. patent application Ser. No. 08/387,676 filed Feb. 13, 1995, now abandoned, which is a continuation-in-part of Ser. No. 08/159,053 filed Nov. 29, 1993 now U.S. Pat. No. 5,389,085, entitled AUTOMATIC NEEDLE PROTECTOR, issued on Feb. 14, 1995, which is a continuation-in-part of Ser. No. 08/016,285 filed Feb. 11, 1993, now U.S. Pat. No. 5,292,314, the disclosures of which are incorporated herein by reference.

STATEMENT REGARDING FEDERALLY SPONSORED RESEARCH

Not applicable.

BACKGROUND OF THE INVENTION

The use of needles for penetrating the body is essential in modern medicine. Their uses include injecting fluids into, or drawing blood or other fluids out of almost any part of the body. The sizes of the needles, and the associated syringe equipment, will vary according to their function.

However, regardless of the size, use, or function, the needle is inevitably a sharp and potentially hazardous object. It should be safely stored, and, more important, safely discarded after any use. This is mandatory at all health facilities, but the facts prove that, with human nature, and overworked, human hospital staffs, used needles will always be found, and will always be a potential hazard.

The potential danger in needles is, of course, in used needles that may have picked up a pathogenic microorganism of some kind from anyone using, or being injected by a needle. Once used, the needle must be considered contaminated, and, even if the risk is microscopic, it is a potential threat to the next person who, accidentally or otherwise, comes in contact with the needle. With certain deadly viruses living in a few human beings today, no gamble, however microscopic, is tolerable.

All hospitals, and other users of needles, have established systems and rules for the control of the use of and disposition of needles. Most of these are almost foolproof, and restrict the use of needles to well trained professional personnel. However, it is now these valuable people who are at risk from the casual, unprotected needle that may have been accidentally overlooked and is just lying around. Contact with this needle could be equally unpredictable. One could be standing, sitting, or in motion of any kind, and the contact could be with any part of the body.

Again, the risk of a trained medical technician coming in contact with a stray needle—let alone its sharp end—should be negligible, and, that this particular needle might be infected, would be another very remote possibility, but, where that possibility, however remote, could be lethal or harmful in any way, the stakes are still too high.

The obvious, and basic, solution to the problem would be to have a safety shield or cover over the needle, before and after it is used. This is done quite effectively in several of the systems, but, in most of the systems, it relies on the human function of putting on, taking off, and putting the safety shield back on before discarding the needle in the required manner.

What is needed is a safety shield that is part of the needle structure and that is locked in a position that covers and protects the sharp end of the needle. There must be a means for uncovering the safety shield, and activating the device for use, at least one time, but the safety shield must be returned, automatically, to its locked, protective position immediately after use.

SUMMARY OF THE INVENTION

A surgical needle projects from the lower end of a tubular structure. A protective cover, or shield, in the form of a tubular sleeve, slightly larger in diameter than the tubular structure, has an upper end fitting over the lower end of the tubular structure. The lower end of the sleeve completely covers and guards the sharp end of the needle. Elongated, generally axial, entrance and exit slots are formed in the tubular structure, between its lower and upper ends to engage a spring-loaded lug on the underside of the tubular sleeve. This allows the sleeve to move upward, with the lug sliding along the entrance slot of the tubular structure, to uncover the needle. The lug then rotates through a change-over slot, to the exit slot, to be forced downward and lock at the base of the exit slot, to recover and guard the needle. A spring connected between the tubular structure and the sleeve provides a radial torque to urge the lug from the entrance slot, through a change-over slot, toward the exit slot. The spring also provides an axial force to oppose the uncovering of the needle and to urge the sleeve, always, toward its needle-covering and locking position. The upper end of the tubular structure will be provided with a luer, or other fitting to couple the needle assembly to its intended function.

In accordance with the further embodiment of the invention, a tubular mount is provided with a hub attached to an upper end, an open lower end, and an aperture in a side of the mount. The hub has a needle extending from a lower end and a fitting at an upper end for coupling to a barrel and plunger assembly. A protective cover is provided having a diameter smaller than that of the mount so that an upper end of the cover fits inside of the lower end of the mount. The cover has an apertured lower end and is adapted for being in a needle protection position in which the tip of the needle is covered by the cover or a retracted position in which the needle extends through the apertured lower end of the cover to be exposed for use. A lug protrudes from a tab on the cover to engage the aperture in the side of the mount so that, as the cover is moved between the needle protection position and a retracted position, the lug moves in the aperture toward the upper end of the mount. The aperture includes an entrance position adjacent to the lower end of the mount and an armed position radially spaced from the entrance position by an angled portion of the mount. The needle protector is armed by rotating the cover to move the lug from the entrance position along the angled portion and to the armed position. A spring is coupled between the mount and the cover so that when the device is armed, a rotary torque is imparted to the spring. Movement of the cover to a retracted position upon actuation of the device causes the spring to be subjected to a compressive force. The torsional and compressive forces on the spring cause the lug to be urged back to the entrance position, thereby automatically causing the cover to return to the needle protection position.

In accordance with another embodiment of the invention, the needle protector device includes a needle subassembly having a hub from which the needle extends and ribs running axially along the exterior of the hub. The device further includes a tubular mount having an interior tapered channel through which the needle subassembly is guided during assembly. The ribs deflect slightly inward as the needle subassembly is urged through the channel and flare outward slightly once the subassembly has been pushed into the mount to retain the subassembly within the mount by an interference, or press fit attachment. The mount has an aperture for engaging a lug of a protective cover in assembly, as described above.

Protrusions are provided on the interior wall of the tapered channel of the mount to prevent rotation of the needle subassembly relative to the mount. More particularly, rotation of the needle subassembly is prevented by the interference of the protrusions with the ribs on the needle subassembly hub.

A spring coupled between the mount and the protective cover includes a pair of extensions, one extending axially from each end of the spring. In assembly, one of the spring extensions is inserted into an aperture in the mount and the other spring extension is inserted into an aperture in the cover. The cover and mount are then rotated relative to one another in order to torsionally bias the spring. With the cover and mount thus rotated relative to one another, the cover and mount are coupled together by inserting the cover into the lower end of the mount. More particularly, an assembly ramp positioned axially with respect to the entrance position of the mount aperture receives the cover lug. The cover lug rides along the assembly ramp until the lug clears the ramp and enters the mount aperture through which the lug protrudes.

With this embodiment, a needle having an automatic protective mechanism and the ability to be re-armed further includes features facilitating simplified assembly. The press fit attachment of the ribbed needle hub to the tapered channel of the mount eliminates the need for sonic welding or solvent bonding. The axial spring extensions, the spring biasing achieved by rotating the cover and mount relative to one another, and the assembly ramp on the mount provide a simple scheme for biasing the spring in torsion and compression and for coupling the cover to the mount. Additional features include alignment grooves on both the cover and the mount for facilitating alignment between the cover and the mount for use in manual or automated assembly.

In a still further embodiment of the present invention, a needle protector device is operable by movement directly from a locked position to a retracted position without the need for first arming the device. The device includes a mount, to which a needle subassembly is fixed, and a protective cover for the needle telescopically coupled to the mount against the biassing of a compression spring. The protective cover is coupled to the mount by a pair of protruding lugs which engage a pair of channels in the mount. The channels each include an entrance portion adjacent the lower end of the mount and an elongated portion extending at an angle toward the upper end of the mount. When the lug is in the entrance portion, the cover is in a locked needle protection position in which the needle tip is covered. To operate the device, the device is placed against a needle-receiving surface and the mount is simultaneously pushed toward the surface and rotated with respect to the cover, causing the lug to move out of the entrance portion to unlock the cover and travel along the elongated portion of the channel. Upon removal of the needle from the needle-receiving surface, the compression spring biases the cover back over the needle.

These features provide safer actuation and permit a simple, effective, and relatively inexpensive manner of assembly. The spring does not require prebiasing in torsion, simplifying both assembly and operation. The device is safer to operate, since it does not require arming by rotating the cover with respect to the mount which requires placing the hand close to the opening through which the needle extends. Operation is simpler in that the device needs only to be placed against a needle-receiving surface before actuating the device. The device is safer in that actuation requires simultaneously pushing the device against the needle-receiving surface and turning the mount with respect to the cover, thereby reducing the likelihood of inadvertent actuation. Notably, actuation cannot occur unless the device is compressed against the action of the spring, i.e., by placing it against a needle-receiving surface. The safety features of the device are further enhanced by the automatic return to the locked position upon removal from the needle-receiving surface.

BRIEF DESCRIPTION OF THE DRAWINGS

The foregoing features of this invention, as well as the invention itself, may be more fully understood from the following description of the drawings in which:

FIG. 25 is a cross-sectional, exploded view of a still further embodiment of the present invention;

FIG. 26 is a cross-sectional view of the device of FIG. 25 in the assembled, locked position;

FIG. 27 is a cross-sectional view of the device of FIG. 25 in a retracted position;

FIG. 28 is an end view of the protective cover of the device of FIG. 25;

FIG. 29 is a cross-sectional view of the protective cover taken along line A—A of FIG. 28;

FIG. 32 is a cross-sectional view of a still further embodiment of a mount and needle subassembly adapted for coupling to a protective cover of the type shown in FIG. 25.

DETAILED DESCRIPTION OF THE INVENTION

Figure 1:
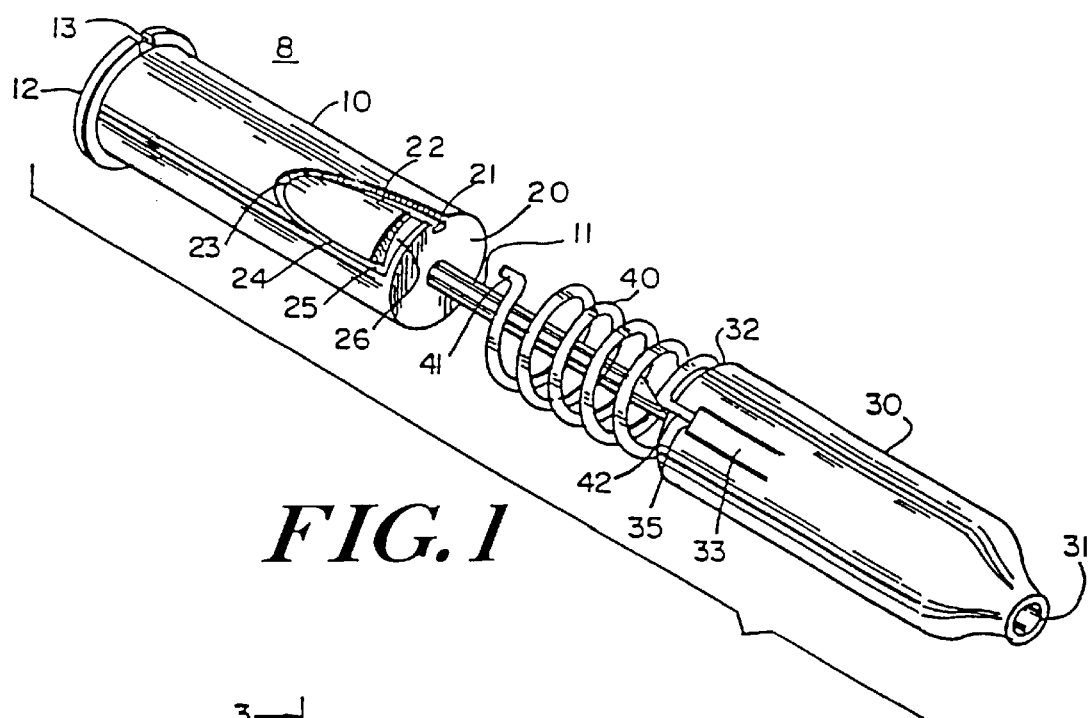
FIG. 1 shows an isometric, exploded view of the device.

Referring now more particularly to FIG. 1, and isometric view of the basic device 8 is shown in an exploded form to clearly illustrate the elements that interact to provide the automatic, safety, needle protector. An upper portion 10 is a hollow tubular mount that supports a needle 11 at one, lower end 20. The other, upper end has a flange 12, with a notch or slot 13 to accommodate the upper end 41 of a spring 40 in a manner that will be described later.

Figure 3:
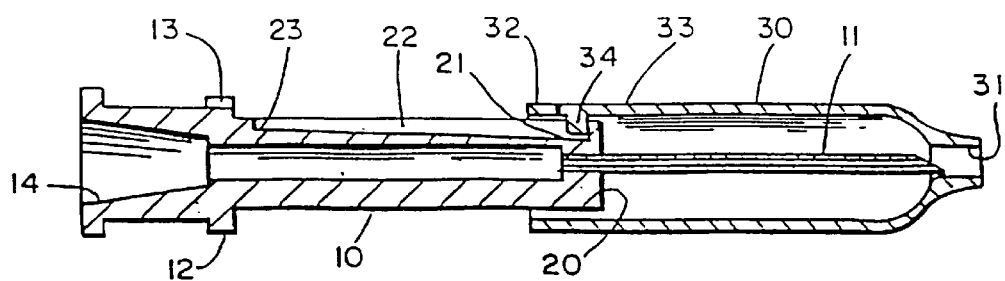
FIG. 3 shows a cross section of the device along the lines 3—3 of FIG. 2.

This other, upper end of the tubular sleeve 10 will, normally, include one of the conventional couplings for a syringe, such as the luer fitting 14 shown in FIG. 3. This has been omitted here, and in other drawings, for simplicity. Other fittings for similar functions can also be accommodated.

The needle 11 is mounted in the center of the base 20 at the lower end of the tubular needle mount 10, in a well known manner. The sharp point, or tip, of the needle will be protected by a cover or sleeve 30.

This exploded view shows, quite clearly, typical slots in the needle mount that control the position and function of the protective cover 30 for the needle in a manner that will be illustrated in the other figure and described in more detail in due course.

These typical slots include an opening 21 for an elongated starting or entrance slot 22 that goes up to a change-over slot 23, that leads to an elongated exit slot 24 that ends in a locking ledge 25 that automatically locks the protective cover 30, with its lower end 31 over the needle.

The protective cover 30 has an opening 31 in its lower end that the needle can extend through when its inner lug 34 is moving through the slots 22, 23, and 24, and the device is in use. The other, upper end 32, as noted earlier, is open and forms the sleeve that fits loosely around the tubular needle mount 10. A notch 35 may be provided in the upper end 32 of the sleeve 30 to support the lower end 42 of the spring 40, as shown. This spring 40 provides the automatic operation of the protective cover.

Figure 4A:
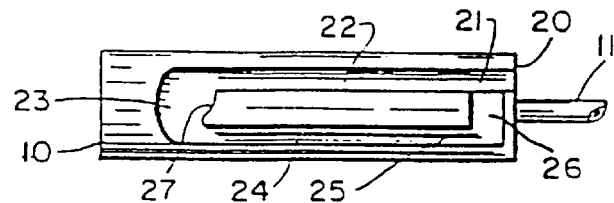
FIG. 4A shows a top view of the needle mount normal to the lines 4—4 of FIG. 2.
Figure 4:
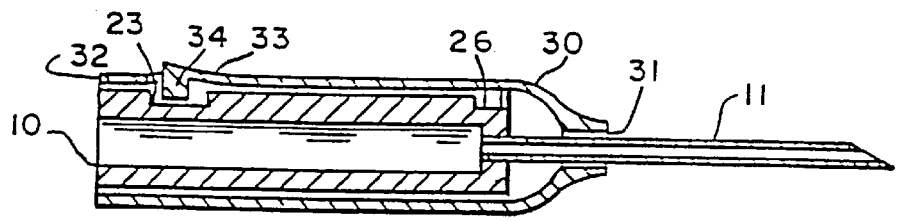
FIG. 4 shows a cross section of the device along the lines 4—4 of FIG. 2.
Figure 5:
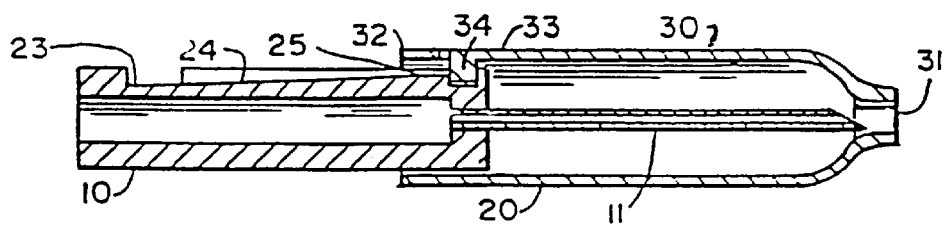
FIG. 5 shows a cross section of the device along the lines 5—5 of FIG. 2.

Another, flat spring 33 actuates a lug or cam 34, seen in FIGS. 3, 4, and 5, that rides in the slots 21 through 26 for the automatic control of the protective sleeve.

The spring 40 would, in operation, fit loosely over the tubular needle mount 10. The upper end clip 41 would fit into, and may be secured in the notch or slot 13 of the flange 12. The lower end clip 42 would fit into the notch or slot 35, as noted earlier, and may also be secured therein.

Figure 2:
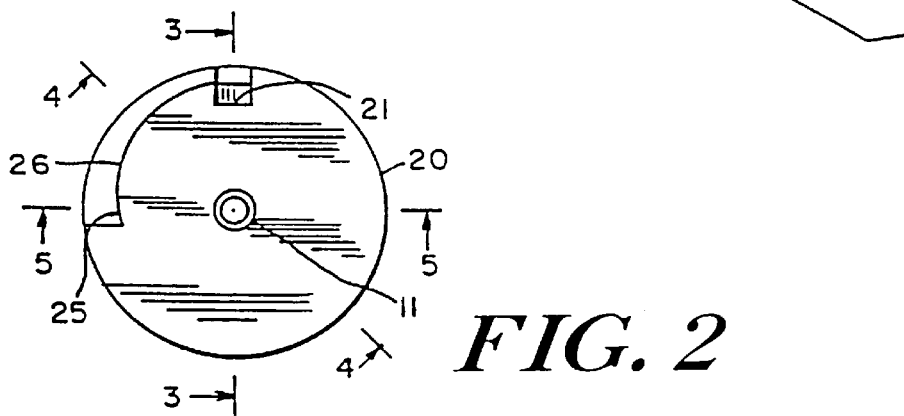
FIG. 2 shows a plan view of the needle mount.

FIG. 2 shows a plan view of the lower end 20 of the tubular needle mount, seen along the needle 11. This, more clearly, shows the opening 21 for the start of the lug 34, mounted on the underside of the spring 33, through its automatic locking path. This also shows the ledge 25, at the end of the slot 24, that secures the lug or cog 34 and locks the protective cover 30, with its end 31 well over the sharp end of the needle. Actually, the needle can be reactivated by rotating the sleeve 30, and moving its cog up the ramp 26 to drop back into the starting slot at 21.

FIG. 3 shows a cross section of the device along the lines 3 3 of FIG. 2. This shows the protective sleeve 30 with its upper end 32 over the tubular mount 10, its lower end 31 covering and protecting the sharp end of the needle 11, and its cog 34 started in the opening 21. The slot 22 will guide the cog to the changeover slot 23, and may raise it partially in the process. This figure also shows the flange 12, with the notch or slot 13 to accommodate the upper, outer end clip 41 of the spring 40.

The spring 40 is not shown in this and the subsequent drawings for simplicity and clarity in illustrating the other, most important elements of the safety cover, and their complex functions.

A typical luer fitting 14 is illustrated in this figure. Obviously this—or a similar coupling would be necessary for coupling this safety device to any conventional unit that needs a hypodermic needle, which is the normal function of this device.

FIG. 4 shows another cross section of this device along the lines 4—4 of FIG. 2. This shows the protective sleeve-or cover 30 drawn to the upper end of the tubular mount 10. This shows the cog 34, on the flat spring 33 of the sleeve 30 in the cross-over slot 23, and the needle fully exposed. As in all of these figures, similar elements are similarly numbered. The luer fitting 14 is, again, omitted for simplicity in this and the rest of these drawings.

FIG. 4A is a top view of the tubular mount 10 for mounting the needle 11, normal to the lines 4—4 of FIG. 2, and is added to illustrate another variation of the slots 21 through 26. This is the version that is, actually, used in the drawings 3, 4, and 5. To this has been added a notch 27 along the cross-over 23. This would hold the lug 34 against the pressures of the spring and would allow the protective cover 30 to be held with the needle exposed, if necessary, while it is being inserted or used. Subsequent movement or use of the cover 30 would complete the cycle, along the path of the lug 34, to the slot 24 and to the ledge 25, to lock the protective cover 30 in its safe position.

This figure also shows more depth to the cross-over 23. Actually this cross-over could extend from near the top of the slots to near the lower end of the mount. This could provide the essential, automatic safety locking of the sleeve with a minimal penetration of the needle, which might be advisable in many cases.

FIG. 5 is another cross section of the device, along the lines 5—5 of FIG. 2, and this shows the protective cover at the end of its cycle, with the lug 34 of the protective cover system locked against the ledge 25, and the end of the cover 31 well over the tip of the needle 11.

This shows the cross-over slot 23 and the slot 24 with its ramp that carries the cog 34 up until it passes over the ledge 25, where the pressure of the spring 33 depresses the lug 34 to lock the safety shield in its safe condition. The spring 40, of course, in its axial pressure urges the cover and lug along the slot 24 to the locking position.

Figure 6:
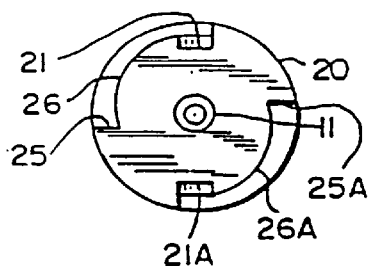
FIG. 6 shows a plan view of another variation of the needle mount.

FIG. 6 is another plan view of the bottom 20 with a variation of the needle holder, again in line with the needle 11. This shows an additional slot 21A, a ledge 25A, and a resetting slope 26A to accommodate an additional lug, not shown, to double the strength and the safety of the automatic locking function. Additional combinations of slots and lugs could, obviously, be added for additional strength and safety.

In operation, the device would normally be assembled with the elements of FIG. 1 compressed to the profile of FIG. 3. For example, the spring 40 would fit loosely over the tubular needle mount 10, with its upper end 41 seated in the notch 13 of the mount. This holds the protective cover, or sleeve 30 with its outer end 31 covering the sharp end of the needle 11, and its inner end fitting over the lower end 20 of the tubular needle mount. The lower end of the spring 42 is secured into the slot 35 of the protective cover, to hold the cog 34, mounted in the cover, in line with and against the ledge 25 so that the protective cover cannot be pushed back to expose the sharp end of the needle, whether it has been used or not.

When it is time to use the needle, for any reason, the needle mount 10 can be coupled to an appropriate syringe, or other device at its fitting 14. The cover or sleeve 30 can then be rotated—in this case clockwise—to move the cam 34 up the slope 26 to drop into the opening 21 at the start of the slot 22. This puts a rotary torque on the spring 40 which urges the cam back to the angle of the slot 24, which leads back to its locking ledge 25. However, the only way the cam can get back from its starting position 21 is to slide along the slots 22, 23, and 24 to be lifted and dropped back into the locking position at 25.

In other words, once the protective cover or sleeve is armed or cocked, the spring exerts a rotary pressure on the cover to urge the cam back towards its exit slot 24, and its locking position at 25. The spring also exerts an axial pressure on the cover to hold it in position over the sharp end of the needle until it is being used. The spring is then compressed axially to expose the needle for use, while moving the cam along the slots 22 and 23. Then the cam can only follow the slot 24 to return the cam, automatically, by the combined rotary and axial pressures of the spring, to its safe, locking position over the ledge 25, where the sharp end of the now used needle is automatically and permanently protected against accidental penetration of anything or anybody.

The spring, here, has this double function, and insures the automatic operation of the safety protective cover. The spring may be made of any springy material, from metal to plastic, and may be of any suitable, functional shape. Actually, the spring 40 may be molded as part of the sleeve 30, when suitable materials are chosen.

The materials chosen would presumably be of plastic. Both the protective cover, with or without the spring, and the tubular mount for the needle would, obviously, be molded for mass production and cost effectiveness. While the safety of medical workers is of prime importance, the cost of providing safety should be reasonable. The object of this invention is to provide the best possible, and almost foolproof protection, at a minimal cost.

It should be noted that these units are disposable—as must all needle mounts be—but these are permanently protected wherever they are disposed. The law, of course, meticulously requires a very special disposal of all medical wastes, which means there is no problem. However, sadly, human error, indifference, or duplicity loads our beaches and other facilities with medical wastes.

The mount 10 that physically supports the needle, which is the essential element of this device, is standard, and similar to many standard needle holders, that couple a needle to a luer, or other fitting, for its ultimate use. However, this unit may be slightly longer to accommodate the motion of the protective sleeve over the needle and mount.

The length of the sleeve, and the mount, will vary with the length and size of the needle, which will vary according to its many uses. The size and shape of the device will vary, along with the ultimate use. This will, again, be a function of the size, and length of the needle. The smallest possible would, of course, be most desirable.

A solid, thin cap over the base 20, at the lower end of the mount would be very easy to attach, and desirable for locking the lug in both directions. This would prevent the sleeve from being pulled off the needle mount, as well as from being pushed in to expose the needle, which would virtually eliminate exposure of the needle in any manner. In this case, a secondary means for raising the spring 33 would be needed to fit the lug 34 in either the starting slot or the locking ledge. This could also avoid the need for, or use of the slope 26, which could be eliminated, to avoid the accidental rotation of the sleeve to arm the device.

The protective sleeve 30, as well as most of the rest of the device, would be of plastic for ease of manufacture. The sleeve should be as small as practical, and quite transparent to allow the needle to be seen and controlled. The opening at 31 may be the full size of the sleeve, or may be just large enough, as shown, for the needle to fit through.

Figure 7:
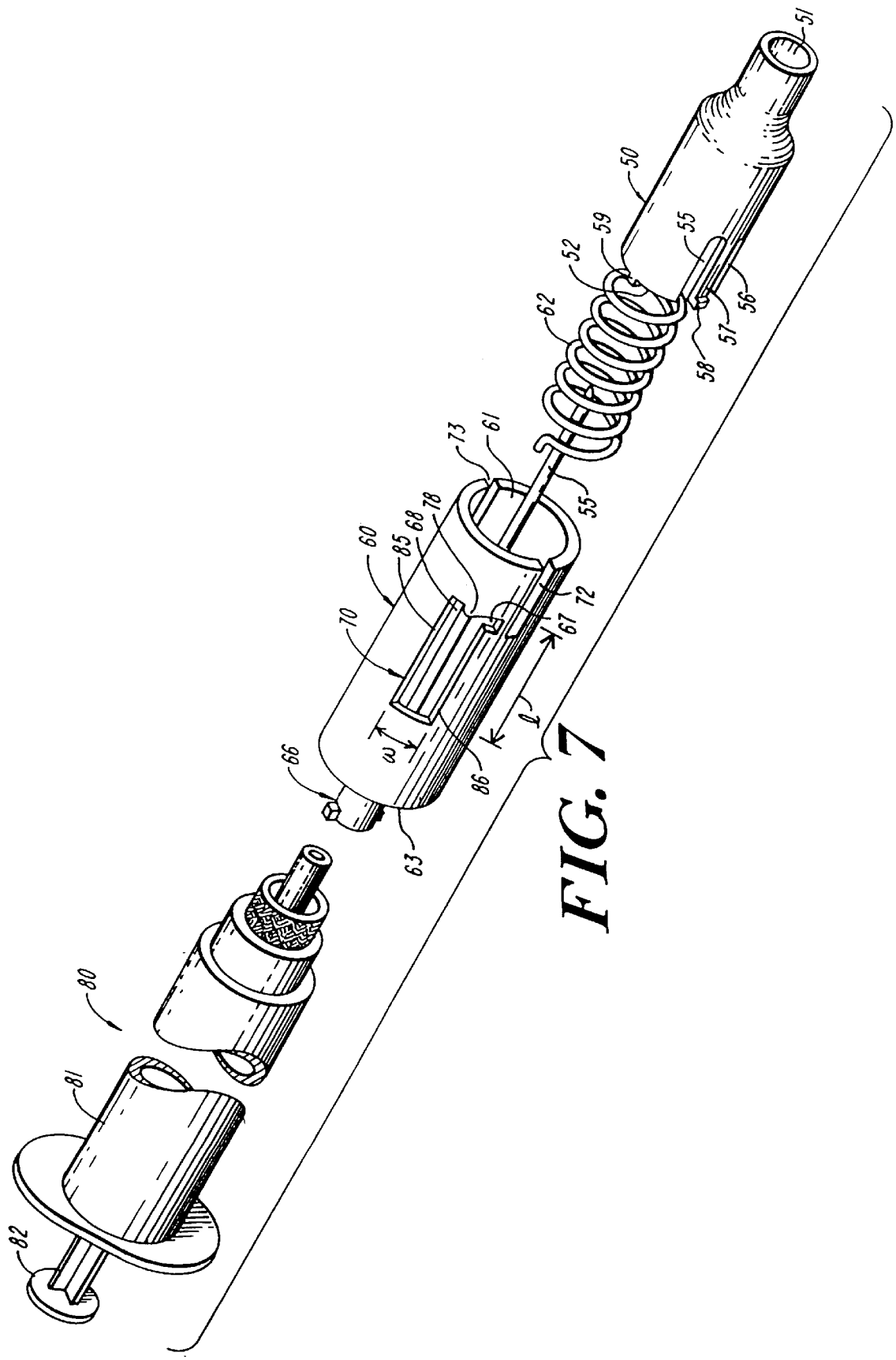
FIG. 7 shows an isometric, exploded view of a further embodiment of the invention with an exemplary barrel and plunger assembly.
Figure 8:
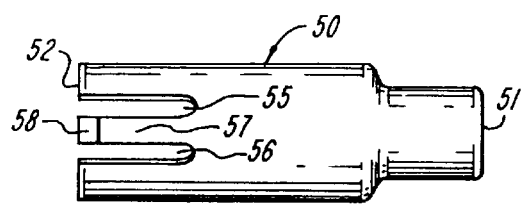
FIG. 8 shows a side view of the protective cover of the device of FIG. 7.

Referring to FIG. 7, a further embodiment of the invention is shown to include a protective cover, or sleeve 50 which fits inside a hollow, tubular mount 60. The protective cover 50 has an opening 51 at its lower end of a diameter suitable for permitting a needle 55 to extend therethrough during use. The diameter of the upper end 52 of the cover 50 is smaller than that of the mount 60 into which the cover extends. The protective cover 50 includes a pair of notches 55, 56 at the upper end 52 which are spaced to provide a cantilevered tab 57 therebetween. An upper end of the tab 57 has a lug 58 protruding therefrom, as shown also in FIG. 8. The cantilevered arrangement of tab 57 provides the tab with a resiliency which is advantageous during assembly of the device, as will be described.

Figure 9:
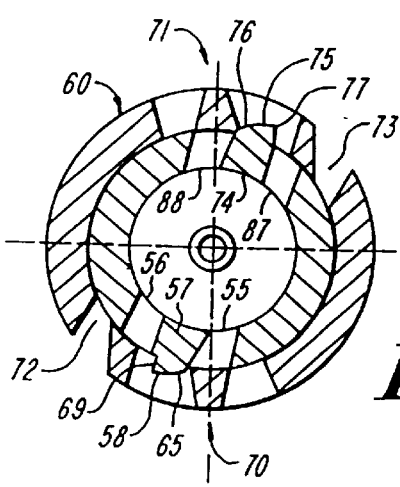
FIG. 9 shows a cross sectional view of the assembled device of FIG. 7.

Referring also to FIG. 9, a second, like tab 74 and a second pair of notches 87, 88 are provided in the upper end of the cover 50 at opposing locations with respect to the tab 57 and notches 55, 56, respectively. The second tab 74 has a lug 75 protruding therefrom, like lug 58. Each of the lugs 58, 75 has a tapered edge 65, 76, respectively, which further facilitate assembly of the device, and a flat edge 69, 77, as shown.

A spring 62 provides automatic operation of the protective cover 50 in response to axial and torsional forces applied during operation, as will be described. Suffice it here to say that the spring 62 is coupled between the protective cover 50 and the mount 60 with a lower end of the spring 62 attached to the cover 50 and an upper end attached to the mount 60. Specifically, the lower end of the spring has a hook portion which extends through a loop 59 on the upper end 52 of the cover 50.

The hollow, tubular mount 60 has an open lower end 61 for receiving the upper end 52 of the protective cover 50 and an upper end 63 coupled to a hub 66. More particularly, the upper end 63 of the mount 60 has an opening for receiving the hub 66, as can be seen in the cross-sectional views of FIGS. 11 and 12. The hub 66 supports the needle 55 at a lower end and has a coupling, or fitting, such as a luer fitting, at an upper end for mating with a conventional syringe barrel and plunger assembly. One exemplary assembly 80 is shown in FIG. 7 to include a barrel 81 and plunger 82. Various means for fastening the hub 66 to the mount 60 are suitable, such as sonic welding. Both the barrel and plunger assembly 80, as well as the hub and needle assembly 66 may be conventional, commercially available assemblies. The spring 62 is secured to the upper end of the mount 60 by locating the upper end of the spring 62 in a hole 64 in the upper end 63 of the mount 60 (see FIGS. 11 and 12).

Referring also to FIG. 9, the tubular mount 60 has two apertures 70, 71 and a pair of slots 72, 73, each one corresponding to one of the apertures 70, 71, respectively, and being spaced therefrom. Slots 72, 73 facilitate assembly of the device, as will be described. Each of apertures 70, 71 has a width labelled "w", a length labelled "l", and permits the protective cover 50 to be in a needle protection position, an armed position, or in one of a plurality of retracted positions during use of the device when the needle 55 is exposed.

Considering exemplary aperture 70 and slot 72, the lug 58 engages the aperture 70 and is moveable within the constraints of the aperture 70 to provide the cover 50 in the needle protection position, the armed position, or a retracted position. That is, the lug 58 protrudes through the aperture 70, slightly beyond the inner diameter of the mount 60, so that the edges, or walls of the aperture 70 restrict the movement of the lug 58 and cover 50. However, preferably, the lug 58 does not protrude beyond the outer diameter of the mount 60 in order to prevent potential undesirable interference with actuation of the device.

The needle protection position of the cover 50 corresponds to the lug 58 being located in a first, entrance position 67 of the aperture 70. The armed position corresponds to the lug 58 being in a second, armed position 68 of the aperture 70. When the cover 50 is in a retracted position, the lug 58 is located above the entrance and armed positions 67, 68 and toward the upper end of the mount 60 between an entrance wall 85 and an exit wall 86 of the aperture 70. The entrance and armed positions 67, 68 of the mount aperture 70 are radially spaced by an angled portion 78 of the mount 60. While the operation of the device is described with respect to exemplary lug 58 and aperture 70, it is understood that aperture 71 has like features for engaging corresponding lug 74.

The mount 60 and the protective cover 50 may be comprised of any material having suitable strength and other desired characteristics, such as plastic. Additionally, the mount 60 and cover 50 may be manufactured by any conventional technique, such as injection molding. Preferably, the cover 50, and at least the lower end 51 thereof, is made from a transparent material so that the tip of the needle 55 is visible in order to facilitate proper insertion into a needle receiving surface, such as a patient's arm. Spring 62 may be made of any suitable material providing a spring characteristic, such as metal or plastic. It should be understood that the selected materials and method of manufacturing the components of the device will vary in accordance with, inter alia, application requirements and cost considerations.

In assembling the device, mount 60 is fastened to the hub 66 as noted above, such as by a sonic welding process. The upper end of the spring 62 is positioned in the hole 64 at the upper end 63 of the mount 60 and the lower end of the spring 62 is attached to the cover 50 and specifically, to the loop 59. With the spring 62 thus coupled between the mount 60 and the cover 50, the cover 50 is guided into the larger diameter mount 60 with tabs 57, 74 aligned with corresponding slots 72, 73. Once the cover 50 cannot be inserted further into the mount 60 (i.e., once lugs 58, 75 contact the upper ends of the slots 72, 73), the cover 50 is rotated clockwise. Upon such rotation of the cover 50, the cantilevered tabs 57, 74 are deflected slightly inward toward the inside of the mount 60. This rotation of the cover 50 is facilitated by the tapered edges 65, 76 of the lugs 58, 75, respectively.

Figure 10:
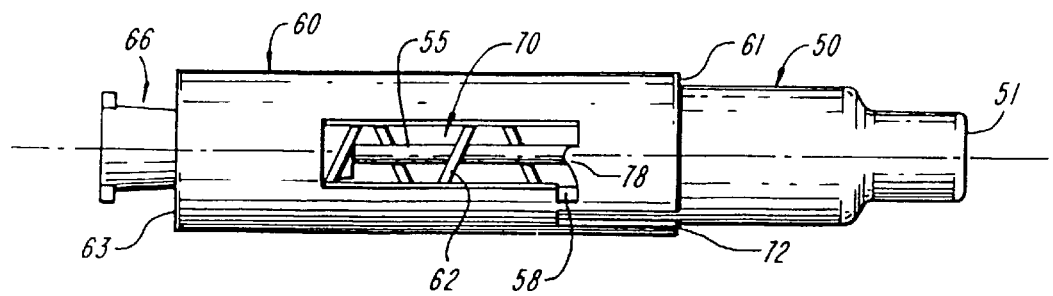
FIG. 10 shows a side view of the assembled device of FIG. 7.

Considering exemplary slot 72, aperture 70, and lug 58, once the lug 58 enters the entrance position 67 of aperture 70, the cover 50 is prevented from rotating counterclockwise due to the flat edge 69 of the lug 58 contacting the side of the entrance position 67 of the mount 60 adjacent to the slot 72. The assembled device is shown in FIG. 10 with the lug 58 positioned in the entrance position 67 of the aperture 70. In this position, the protective cover 50 extends over the tip of the needle 55 and cannot be pushed straight back to expose the needle 55 since the back wall of the entrance position 67 prevents such movement of the lug 58. With the cover 50 disposed in this needle protection position, the spring 62 is in a partially compressed state. Additionally, the spring 62 is subjected to a slight rotary torque, or torsional force, as a result of the rotation of the spring 62 as the cover 50 was rotated to move the lug 58 from the slot 72 to the entrance position 67.

When use of the needle 55 is desired, the hub 66 is coupled to a conventional syringe barrel and plunger assembly, such as the exemplary assembly 80 shown in FIG. 7. The upper end of the hub 66 has a fitting, such as a luer fitting, for this purpose. Thereafter, the device may be armed, or cocked, in preparation for use by rotating the cover 50 clockwise which causes the lug 58 to move along the angled portion 78 of the mount 60 that separates the entrance position 67 from the armed position 68. As the lug 58 clears the angled portion 78, an audible click occurs, indicating to the user that the device is armed and ready for use. By moving the lug 58 to the armed position, an additional rotary torque is exerted on the spring 62 which,, upon actuation of the device, urges the lug 58 back to the entrance position 67.

Figure 11:
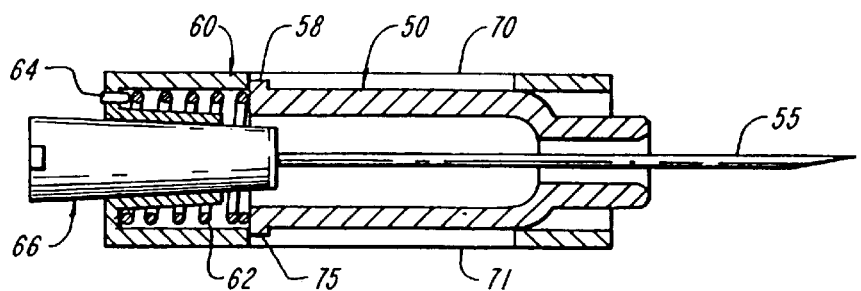
FIG. 11 shows a cross sectional view of the assembled device of FIG. 7 with the protective cover in a retracted position.
Figure 12:
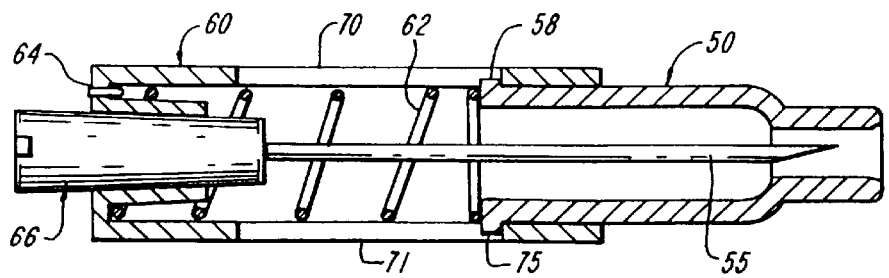
FIG. 12 is a cross sectional view of the assembled device of FIG. 7 with the protective cover in a needle protection position.

As the lower end of the cover 50 is pushed against a needle receiving surface, the cover 50 is forced further inside the mount 60, as shown in the view of FIG. 11. Such actuation of the device causes the spring 62 to be subjected to an additional axial, compressive force, as is apparent from the view of FIG. 11, and causes the lug 58 to move from the armed position 68 along the entrance wall 85 of the slot 70 and toward the upper end of 63 of the mount 60.

The torsional and compressive forces exerted on the spring 62 urge the protective cover 50 back to the needle protection position in which the lug 58 is located in the entrance position 67. Thus, upon removal of the needle 55 from the receiving surface, the protective cover 50 automatically moves to the needle protection position in which the needle tip is covered. Specifically, the rotary torque on the spring 62 causes the cover 50 to move radially, rotating counterclockwise so that the lug 58 contacts the exit wall 86 and the compressive force on the spring 62 causes the cover 50 to move outward from the mount 60 to the needle protection position shown in FIGS. 10 and 12. It is noted that once the lug 58 has returned to the entrance position 67, the device may be reactivated by re-arming the device for further use. That is, once the lug 58 has returned to the entrance position 67, the device can be re-armed by rotating the cover 50 clockwise which causes the lug 58 to move along the angled portion 78 of the mount 60 separating the entrance position 67 and the armed position 68, in the manner described above.

In view of the above described operation of the device, it should be understood that the dimensions of the apertures 70, 71 may be varied in accordance with a particular application. For example, a longer needle 55 may require that the aperture 70 have a greater length "l" to permit a desired exposure of the needle 55. Additionally other device dimensions, such as those of the mount 60 and the cover 50, may be readily varied as required in a particular application.

While the embodiment of FIGS. 7–12 is shown to have two opposingly disposed tabs 57, 74, apertures 70, 71, and slots 72, 73, it should be appreciated that a single tab, aperture, and slot arrangement may be suitable in certain applications.

The needle protector arrangements described herein are useable with conventional syringe barrel/plunger assemblies, such as the exemplary assembly 80 of FIG. 7, so that inventory of such assemblies need not be discarded and replaced in order to use the described devices. Additionally, by modifying the mount 10 to provide slots 22–26 (FIGS. 1–6) and the mount 60 to provide apertures 70, 71 (FIGS. 7–12), the advantages of the present needle protector embodiments are achieved without requiring additional parts.

Figure 13:
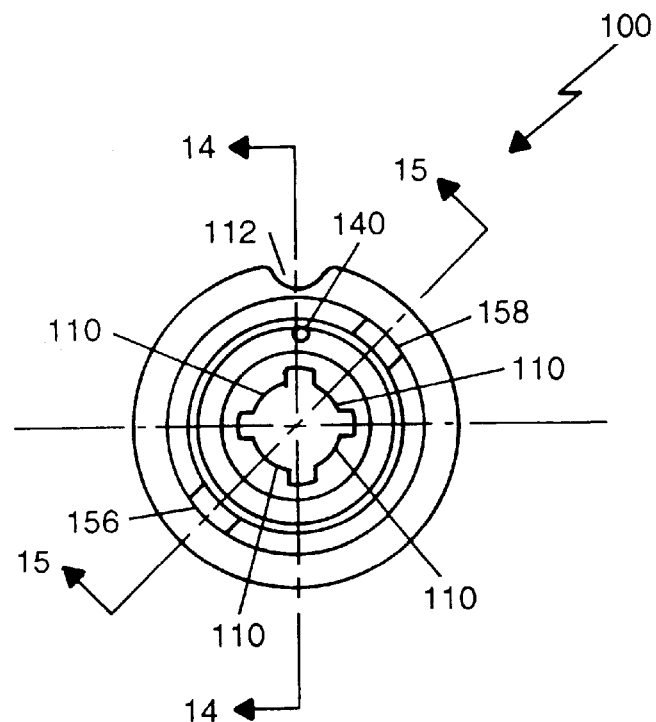
FIG. 13 is an end view of an alternate embodiment of the needle protector mount.
Figure 14:
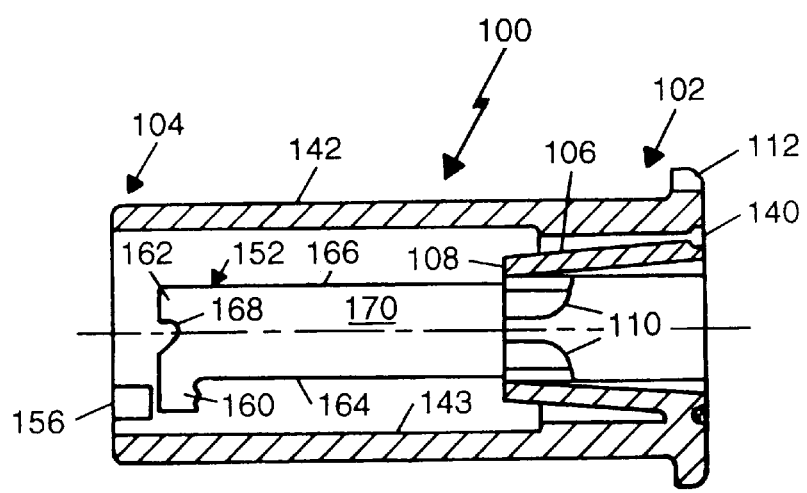
FIG. 14 is a cross sectional view of the mount of FIG. 13 taken along line 14—14 of FIG. 13.
Figure 15:
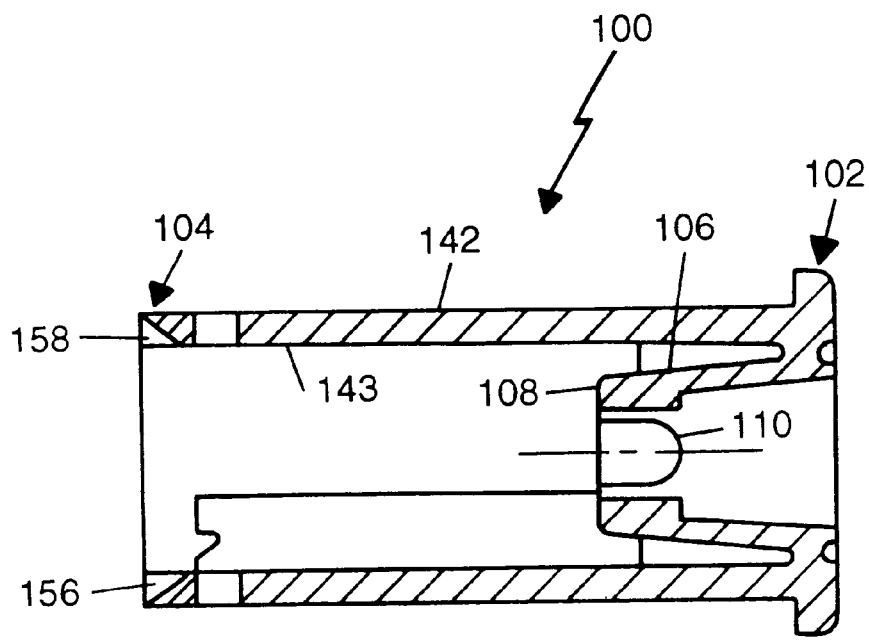
FIG. 15 is a cross sectional view of the mount of FIG. 13 taken along line 15—15 of FIG. 13.

Referring to FIGS. 13–15, various views of an alternate needle protector mount 100 are shown. FIG. 13 is an end view of the mount 100. FIG. 14 is a cross-sectional side view of the mount 100 taken along line 14—14 of FIG. 13 and FIG. 15 is an alternate cross-sectional side view of the mount 100 taken along line 15—15 of FIG. 13.

The mount 100 is substantially cylindrical, or tubular in shape and has an upper end 102 and an open lower end 104. An interior channel 106 extends from the upper end 102 of the mount to terminate at a terminal end, or edge 108. The channel 106 is tapered such that the diameter of the channel 106 at the terminal edge 108 is reduced relative to the diameter of the channel 106 adjacent the upper end 102 of the mount 100. During assembly, a needle subassembly, such as that shown in FIG. 16, is coupled to the mount 100 by insertion into the tapered channel 106.

Figure 16:
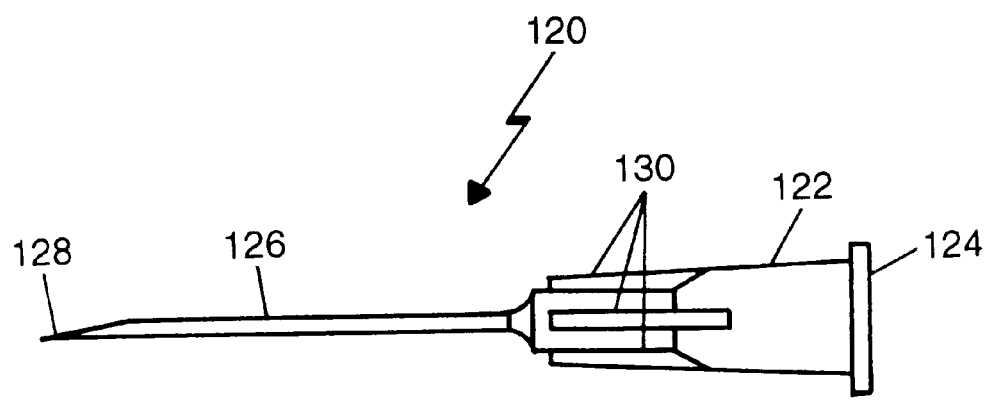
FIG. 16 is a side view of a needle subassembly.

Referring also to FIG. 16, a needle subassembly 120 includes a hub 122 having a luer fitting 124 at a first end and a needle 126 extending from a second end to terminate at a tip 128, as shown. The luer fitting 124 is adapted for connection to a conventional syringe barrel and plunger assembly. The hub 122 has a plurality of ribs 130 extending axially with respect to the needle 126 along the exterior surface of the hub 122.

The hub 122 is comprised of a plastic material having some resiliency. The smallest inner diameter of the mount channel 106, adjacent the terminal edge 108, is slightly smaller than the outer diameter of the hub with the ribs 130. With this arrangement, a press fit attachment of the needle subassembly 120 to the mount in a manner which prevents the subassembly from being readily removed is achieved, as described below.

The needle subassembly 120 may be a conventional, commercially available assembly, as is available from Becton Dickinson & Co. of Rutherford, N.J. In one embodiment, the needle 126 is one inch long. Use of a one inch needle is advantageous, as compared to use of a longer needle, since the shorter needle is less susceptible to bending and thus, is stronger.

The mount 100 has a plurality of stops 110 protruding from the interior walls of the channel 106 into the diameter of the channel 106. Two such stops 110 are visible in the view of FIG. 14 and one stop 110 is visible in the view of FIG. 15. In assembly, the hub ribs 130 are aligned with the mount 100 such that the ribs are disposed between the stops 110. With this arrangement, the stops 110 prevent the needle subassembly 120 from rotating relative to the mount 100 once the subassembly 120 is press fit into the mount 100.

A spring receiving aperture 140 (FIGS. 13 and 14) is disposed in the upper end 102 of the mount 100 between the mount exterior wall 142 and the channel 106, as shown. In assembly, the spring receiving aperture 140 receives one end of a spring, such as the spring 144 shown in FIG. 21 and discussed below.

The mount 100 includes two apertures 152, 154 (only one of which can be seen in the views of FIGS. 14 and 15) and a pair of assembly ramps 156, 158 (FIGS. 13 and 15), each one corresponding to one of the apertures 152, 154. Each of apertures 152, 154 is substantially identical to like apertures 70, 71 described above in conjunction with the embodiment of FIGS. 7–12. As labelled on illustrative aperture 152, each aperture has an entrance position 160, an armed position 162 radially spaced from the entrance position by an angled protrusion 168, and an elongated portion 170 extending toward the upper end 102 of the mount between an entrance wall 164 and an exit wall 166 of the aperture.

Assembly ramps 156, 158 are tapered, or angled portions of the inner wall 143 of the mount 100 extending from the lower end 104 of the mount 100 toward the respective aperture 152, 154, as shown in FIG. 15. The taper of the ramps 156, 158 is such that the wall is thinnest at the portion of the ramp adjacent to the lower end 104 of the mount 100 and is thickest at the portion of the ramp adjacent to the respective aperture 152, 154. The assembly ramps 156, 158 facilitate attachment of the protective cover, such as cover 180 of FIGS. 17–20, to the mount 100 by gradually increasing the deflection of the cover lugs until the lugs enter the respective aperture 152, 154, as described below.

The mount 100 includes an alignment groove 112 shown in FIGS. 13 and 14 extending axially along wall 142. Groove 112 facilitates alignment of the mount 100 during manual or automated assembly of a needle protector including the mount 100 by providing a reference relative to which the mount 100 can be aligned.

Figure 19:
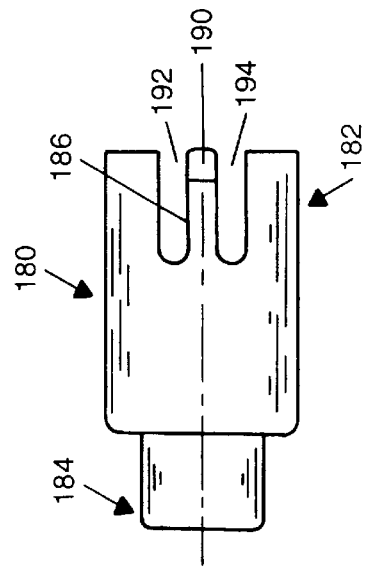
FIG. 19 is a side view of the protective cover of FIG. 17.
Figure 20:
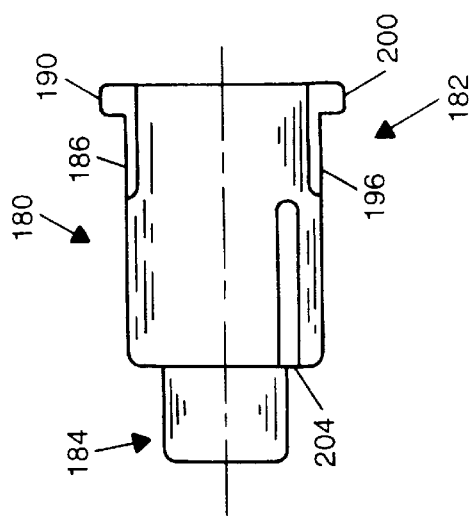
FIG. 20 is an alternate side view of the protective cover of FIG. 17.
Figure 18:
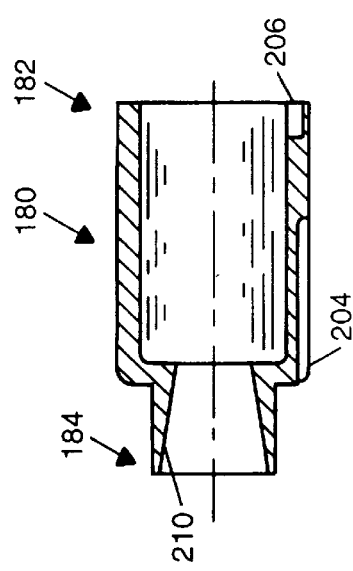
FIG. 18 is a cross sectional view of the protective cover of FIG. 17 taken along line 18—18 of FIG. 17.
Figure 17:
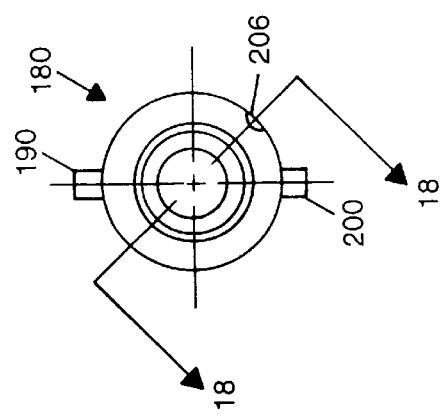
FIG. 17 is an end view of an alternate embodiment of the protective cover.

Referring now to FIGS. 17–20, an alternate protective cover 180 is shown. FIG. 17 is an end view of the cover 180, FIG. 18 is a cross-sectional view of the cover taken along line 18—18 of FIG. 17 and FIGS. 19 and 20 are alternate side views of the cover 180 showing its various features.

The protective cover 180 is substantially cylindrical and has an upper end 182 of an outer diameter slightly smaller than the inner diameter of the lower end 104 of the mount 100, permitting the upper end 182 of the cover 180 to be received within the lower end 104 of the mount 100. A lower end 184 of the protective cover 180 has a reduced diameter relative to the diameter of the upper end 182, so as to prevent a finger from being inserted through the open lower end 184 to contact the needle 126.

The protective cover 180 includes a first pair of notches 192, 194 (FIG. 19) at the upper end 182 which are spaced to provide a cantilevered tab 186 therebetween. An upper end of the tab 186 has a lug 190 protruding therefrom. The cantilevered arrangement of tab 186 provides the tab with a resiliency which is advantageous during assembly of the device, as will be described. The protective cover 180 includes a second pair of notches (not shown) identical to notches 192, 194 which provide a second tab 196 cantilevered therebetween with a lug 200 protruding therefrom. The second tab 196 is positioned 180° from the first tab 186. The first and second lugs 190, 200 are adapted for engaging the first and second apertures 152, 154 of the mount 100 in assembly, respectively. As noted above with respect to the embodiment of FIGS. 7–12, in some applications, a single cover lug and mount aperture arrangement may be suitable.

The mount 100 and the protective cover 180 may be comprised of any material having suitable strength and other desired characteristics, such as plastic. Additionally, the mount 100 and cover 180 may be manufactured by any conventional technique, such as injection molding. Preferably however, the cover 180 is made from a transparent material so that the tip of the needle 126 is visible in order to facilitate insertion into a needle receiving surface, such as a patient's arm.

It is further preferable that the mount 100 and cover 180 be comprised of different materials in order to reduce any sticking therebetween over time. In one embodiment, the mount 100 is comprised of the copolymer styrene-acrylonitrile (SAN) from Monsanto of St. Louis, Mo. and the protective cover 180 is comprised of a polycarbonate from GE Plastics of Pittsfield, Mass.

Additional features of the protective cover 180 include an alignment groove 204 in the exterior surface of the mount 100, as shown in FIGS. 18 and 20. The alignment groove 204 facilitates assembly of the device by providing a reference feature with which the cover 180 can be aligned, or oriented during assembly. The alignment groove 204 permits ready alignment of the cover 180, whether assembly is manual or automated, and can be used in conjunction with the mount alignment groove 112 (FIGS. 13 and 14) to facilitate alignment of the mount 100 relative to the protective cover 180 as the lugs 190, 200 of the cover 180 are directed along the respective assembly ramps 156, 158 of the mount.

A spring receiving aperture 206 is disposed in a wall of the protective cover 180, as shown in FIGS. 17 and 18. Specifically, the spring receiving aperture 206 is positioned at the upper end 182 of the protective cover 180 for receiving an end of a spring, such as spring 144 shown in FIG. 21.

An additional feature of the protective cover 180 is provided by the tapered inner wall portion 210 adjacent to the reduced diameter lower end 184 of the cover 180. The wall portion 210 is tapered such that the wall is thickest at the portion distal from the lower end 184 and is thinnest at the portion adjacent to the end 184, as shown. The purpose of the tapered wall portion 210 is to prevent the needle 126 from gouging the wall of the cover 180 in instances where component tolerances are in a worst case condition. That is, in instances where the inner wall diameter of the mount 100 is at the high end of its specified tolerance range and the outer wall diameter of the protective cover 180 is at the low end of its specified tolerance range, the angled wall portion 210 prevents the needle tip 128 from gouging the cover wall.

Mount apertures 152, 154 permit the protective cover 180 to be in a needle protection position, an armed position, or in one of a plurality of retracted positions to expose the needle 126 during use of the device. The needle protection position of the cover 180 corresponds to the lugs of 190, 200 the cover 180 being located in the entrance position 160 of the respective aperture 152, 154. The armed position corresponds to the lugs 190, 200 being in the armed position 162 of the respective aperture 152, 154. When the cover 180 is in a retracted position, the lugs 190, 200 are located in the respective aperture portion 170, above the entrance and armed positions 160, 162 and toward the upper end 102 of the mount 100 between the entrance wall 164 and the exit wall 166 of the respective aperture 152, 154.

Figure 21:
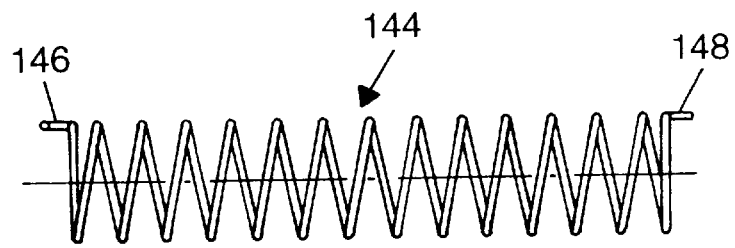
FIG. 21 is a side view of an alternate spring.

Referring to FIG. 21, an alternate spring 144 is shown to include a pair of extensions 146, 148, extending axially from opposite ends thereof. The extensions 146, 148 are adapted for engaging the spring receiving apertures 140, 206 of the mount 100 and, the protective cover 180, respectively. Since the spring 144 has a symmetrical construction, issues regarding orientation of the spring during assembly are advantageously avoided. Spring 144 may be made of any suitable material providing a desired spring constant, such as metal or plastic.

Figure 22:
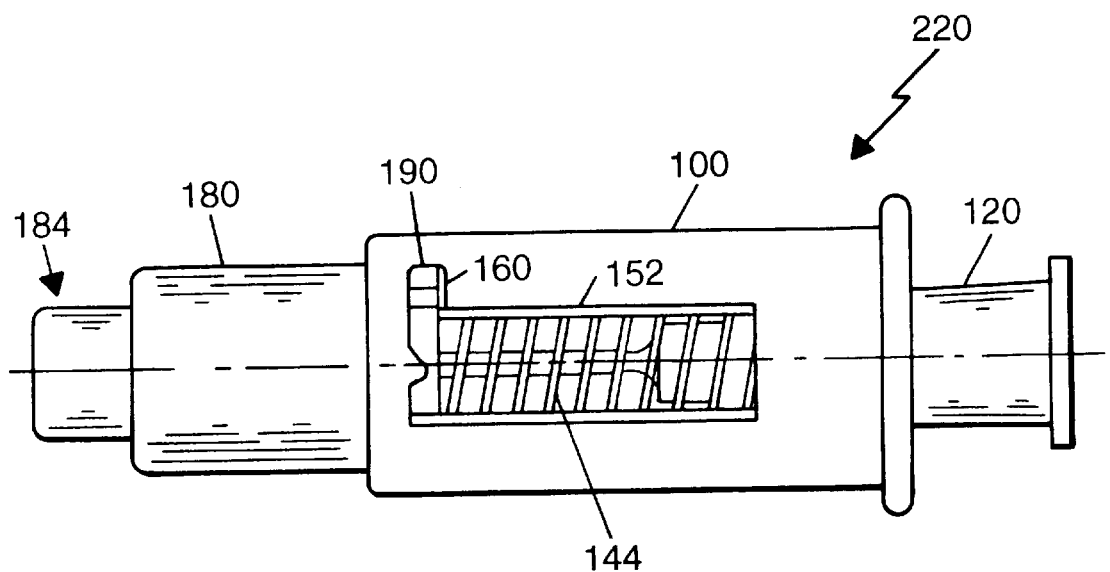
FIG. 22 is a side view of an alternate embodiment of the needle protector device including the mount of FIGS. 13–15, the needle subassembly of FIG. 16, the protective cover of FIGS. 17–20, and the spring of FIG. 21.
Figure 23:
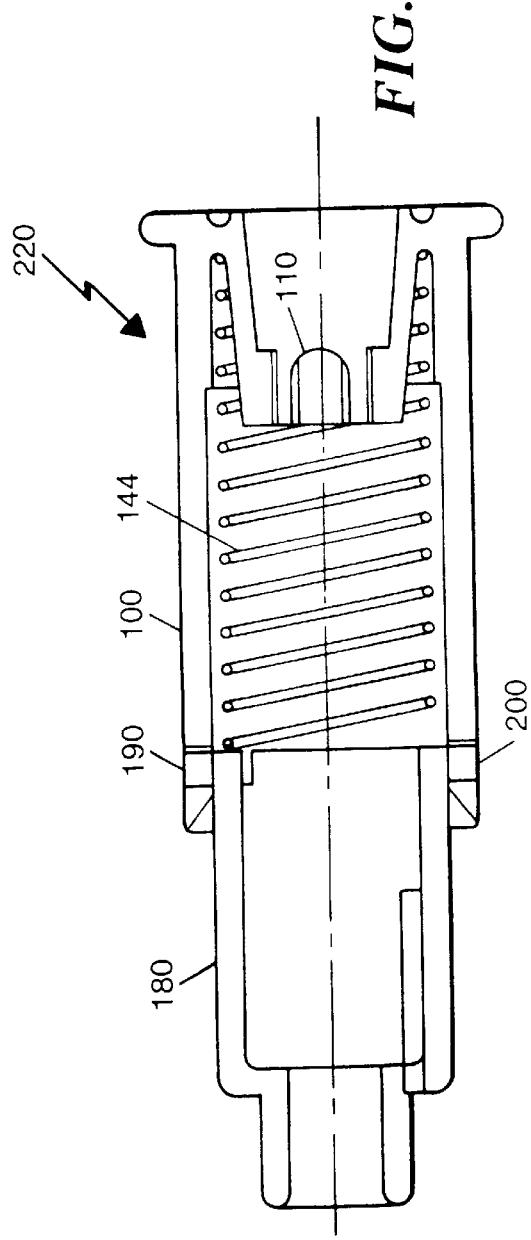
FIG. 23 is a cross sectional view of the needle protector device of FIG. 22 with the protective cover in the needle protection position.
Figure 24:
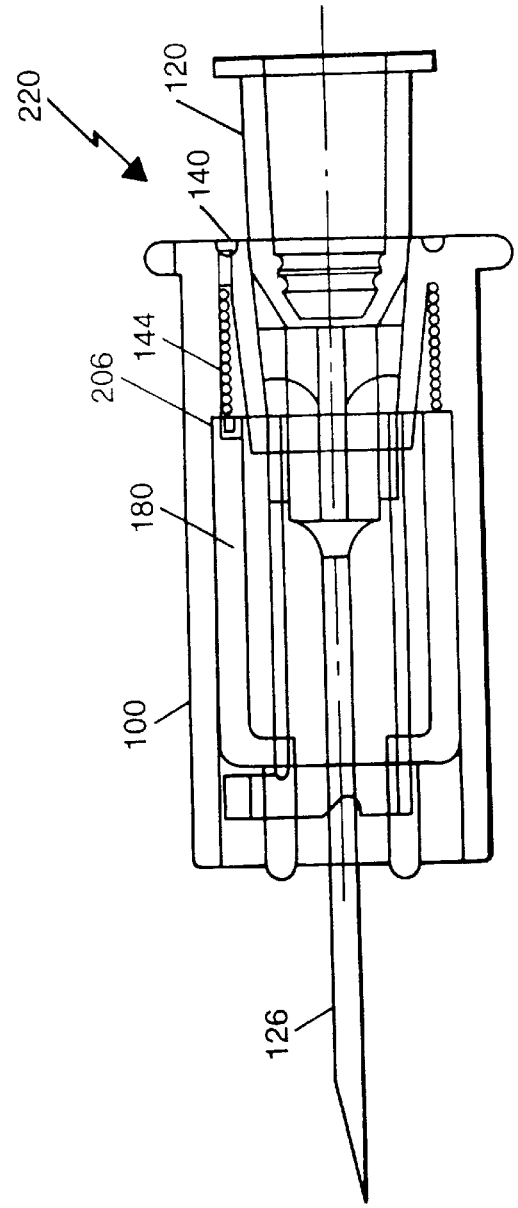
FIG. 24 is a cross sectional view of the needle protector device of FIG. 22 with the protective cover in a retracted position.

Referring now to FIGS. 22–24, an alternate needle protector device 220 is shown to include the mount 100 of FIGS. 13–15, the needle subassembly 120 of FIG. 16, the protective cover 180 of FIGS. 17–20 and the spring 144 of FIG. 21. Specifically, FIG. 22 is a side view of the device 220 with the cover 180 in the needle protection position. Thus, the lugs 190, 200 are in the entrance position 160 of the respective aperture 152, 154, as shown for lug 190 in aperture 152. A cross-sectional view of the needle protector device 220 without the needle subassembly 120 is shown in FIG. 23 and FIG. 24 is a cross-sectional view of the needle protector device 220 with the protective cover 180 in a retracted position, thereby exposing the needle 126 through the reduced diameter lower end 184 of the cover 180.

During assembly, the spring 144 is inserted into the lower end 104 of the mount 100 such that one of the spring extensions 146, 148 extends into the spring receiving aperture 140 at the upper end 102 of the mount, as shown in FIG. 24. With the spring 144 thus positioned, the other spring extension 146, 148 is aligned with the spring receiving aperture 206 of the protective cover 180.

Once the spring 144 is positioned with one extension inserted into the spring receiving aperture 140 of the mount 100 and the other extension inserted into the spring receiving aperture 206 of the cover 180, the mount 100 and the cover 180 are rotated by a multiple of 180° relative to one another to impart a torsional bias on the spring 144. Preferably, the mount 100 and cover 180 are rotated relative to one another by either 180° or 360°. This process can be readily performed with a simple fixture. Having thus biased the spring 144, the cover 180 is inserted into the mount 100.

Specifically, the cover lugs 190, 200 are aligned with a respective assembly ramp 156, 158, the upper end 182 of the cover 180 is inserted into the open lower end 104 of the mount 100. Alignment of the cover 180 and the mount 100 is facilitated by the alignment groove 204 on the cover 180 and the alignment groove 112 on the mount 100. As the cover 180 is urged inside the mount 100, the spring 144 is subjected to a compressional force. The lugs 190, 200 of the cover 180 are deflected inward as they ride along the respective ramp 156, 158, as is permitted by their cantilevered construction. The entrance position 160 of each aperture 152, 154 is located axially adjacent to the respective ramp 156, 158. Thus, as the cover 180 is urged into the mount 100, the lugs 190, 200 overcome the respective ramp 156, 158 and enter the entrance position 160 of the respective aperture 152, 154. Having entered the entrance position 160 of the respective aperture 152, 154, the lugs 190, 200 return to their initial non-deflected positions, thereby causing the lugs 190, 200 to be captured within the respective aperture 152, 154, as shown in the views of FIGS. 22 and 23. The cover 180 is prevented from separating from the mount 100, since the lugs 190, 200 are captured in respective aperture 152, 154. The spring 144 is biased both in torsion and compression once the mount 100 and cover 180 are coupled together in the abovedescribed manner.

Having thus assembled the mount 100, cover 180, and spring 144, the needle subassembly 110 is inserted into the mount 100 from the upper end 102 thereof. As noted above, the ribs 130 of the needle subassembly 120 are aligned with the interior channel 106 of the mount 100 so as to be in axial alignment with regions of the interior channel 106 between the protrusions 110. With the needle subassembly 120 and the mount 100 thus aligned, the subassembly 120 is urged into the mount 100. Since the outer diameter of the hub 120, as defined by the ribs 130, is slightly larger than the inner diameter of the interior channel 106 adjacent to the terminal edge 108, pushing the needle subassembly 120 into the mount 100 provides an interference, or press fit interconnection between the subassembly 120 and the mount 100. This interference fit between the subassembly 120 and tapered interior channel 106 of the mount 100, as well as the flaring of the hub ribs 130 around the forward edge 108 of the housing channel 106 prevents the subassembly 120 from being pulled back out of the mount 100. As will be apparent to those of skill in the art, the needle protector device 220 is suitable for either manual or automated assembly.

The operation of the device 220 thus assembled is substantially identical to the operation of the needle protector embodiment of FIGS. 7–12. That is, when use of the device 220 is desired, the luer fitting 124 of the hub 122 is coupled to a conventional syringe barrel and plunger assembly, such as the illustrative assembly 80 shown in FIG. 7. The device 220 is then armed by rotating the cover 180 clockwise causing the lugs 190, 200 to ride along the angled portions 168 of the respective aperture 152, 154. As the lugs 190, 200 clear the respective angled portion 168, an audible click occurs, indicating to the user that the device 220 is armed and ready for use.

Actuation of the device 220 by pushing the cover 180 against a needle receiving surface forces the cover 180 further inside the mount 100, as shown in FIG. 24. In this retracted cover position, the lugs 190, 200 are positioned in portion 170 of the respective aperture 152, 154. The torsional and compressive forces exerted on the spring 144 during assembly cause the cover 180 to be automatically urged back over the needle tip and thus, cause the lugs 190, 200 to be automatically urged to return to the entrance position 160 of the respective aperture 152, 154. Once the lugs 190, 200 have returned to the entrance position 160, the device 220 can be re-activated or re-armed for further use.

The features of the needle protector 220 of FIGS. 22–24 permit a simple, effective, and relatively inexpensive manner of assembly. Specifically, the press fit attachment of the needle subassembly 120 to the mount 100 provides an effective way of securely attaching the subassembly 120 and mount 100, without requiring the hub 122 to be sonically welded or solvent bonded to the mount 100. The spring 144 simplifies manufacture of the device 220 by its symmetrical construction, thereby eliminating orientation issues. The axial spring extensions 146, 148 are further advantageous in their simplicity of engagement with the mount 100 and cover 180. Furthermore, this axial spring extension arrangement is conducive to biasing the spring 144 in torsion prior to attaching the cover 180 to the mount 100. The alignment grooves 112, 204 of the mount 100 and cover 180, respectively, as well as the assembly ramps 156, 158 of the mount 100 further enhance the ease with which the device 220 is assembled, as described above.

A still further embodiment of the needle protector device is shown in FIGS. 25 through 29. The device 300 comprises a mount 302, a protective cover 304, a needle subassembly 306, and a compression spring 308. The needle subassembly 306 may be like the needle subassembly 120 discussed above.

The mount 302 is substantially cylindrical or tubular in shape and has an upper end 310 and an open lower end 312. An interior collar 314 concentric with an exterior wall 316 of the mount 302 extends from the upper end of the mount to terminate at a terminal end or edge 318. At least a portion 320 of the collar 314 is tapered such that the diameter of the collar at the terminal edge 318 is reduced relative to the diameter of the collar adjacent the upper end 310 of the mount 302. During assembly, the needle subassembly 306, comprising a hub 322 and a needle 323, is coupled to the mount 302 by insertion into the tapered collar 314. The smallest inner diameter of the collar, adjacent the terminal edge 318, is slightly smaller than the outer diameter of the hub 322 of the needle subassembly. With this arrangement, a press fit attachment of the needle subassembly 306 to the mount 302 is achieved with the ribs 326 on the needle subassembly hub 322 flared slightly around the terminal edge 318 of the tapered collar 314 such that the needle subassembly 306 cannot be removed from the mount without effectively breaking the device. In addition, a plurality of stops 324 protrude radially inwardly from the interior walls of the collar 314 for alignment between the hub ribs 326 on the needle subassembly. The stops prevent the needle subassembly 306 from rotating relative to the mount 302 once the subassembly is press fit into the mount. In this manner, the needle subassembly becomes fly attached to the mount, and the device can be actuated, discussed further below, by grasping a conventional syringe barrel and plunger assembly attached to the needle subassembly, rather than by grasping the mount, thereby maintaining the user's hand safely farther away from the region of the needle.

Figure 25A:
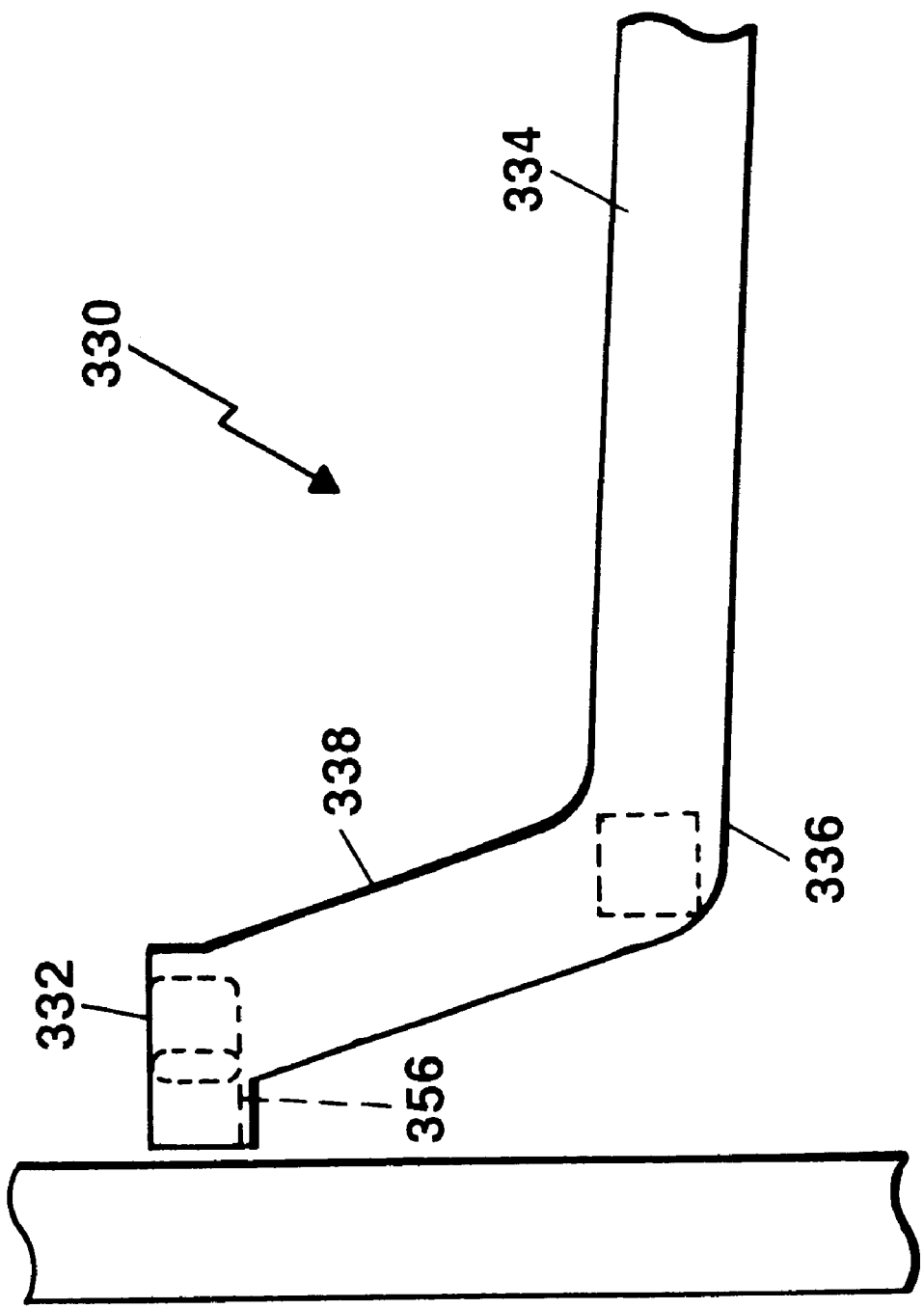
FIG. 25A is an enlarged view of one of the slot-shaped channels of the mount of FIG. 25.

The mount 302 includes two slot-shaped channels 330 (only one of which can be seen in FIGS. 25–27). An enlarged view of one of the slot-shaped channels 330 is shown in FIG. 25A. Each channel 330 has an entrance portion 332 and an elongated portion 334 which are joined by a substantial bend 336. The entrance position 332 includes a detent 356 adjacent to the lower end 312 of the mount 302. The elongated portion 334 extends from the bend 336 toward the upper end 310 of the mount 302 at an angle to the longitudinal axis of the mount. The angle is typically approximately 3°, although the exact angle is not critical to operation of the device, and the optimum angle can be readily determined by those skilled in the art. Typically, two channels 330 are provided, spaced 180° apart circumferentially. However, one or any other number of channels can be provided if desired.

The protective cover 304 is substantially cylindrical and has an upper end 340 of an outer diameter slightly smaller than the inner diameter of the lower end 312 of the mount 302, permitting the upper end of the cover to be telescopically received within the lower end of the mount. A lower end 342 of the protective cover has a reduced diameter relative to the diameter of the upper end 340, to prevent a finger from being inserted through the open lower end to contact the needle 323.

The protective cover 304 includes two U-shaped cut out regions 344 in an intermediate portion 346 to provide two cantilevered tabs 348. An upper end of each tab has a lug 350 protruding radially outwardly therefrom. The cantilevered arrangement of the tabs 348 provides the tabs with a resiliency which is advantageous during assembly of the device, as will be described. Preferably, the tabs are positioned 180° apart circumferentially. The two lugs 350 are adapted for engaging the two channels 330 of the mount, respectively. As noted above with respect to the channels of the mount, one or any other number of cover lugs may be provided, the location and number of lugs corresponding with the location and number of channels.

The lower end 312 of the mount 302 includes a chamfer 305 around its inner circumference. The chamfer facilitates attachment of the protective cover 304 to the mount 302 by gradually increasing the deflection of the cover tabs 348 until the lugs 350 enter the respective channels 330, as described below. Preferably, the angle of the chamfer is slightly greater at locations aligned with the channel entrance portions 332 to define a pair of assembly ramps 352. The differently angled ramps provide a tactile locator for aligning the lugs 350 with the entrance portion 332. In addition, a detent (such as the alignment groove 112 illustrated in FIG. 13) can be provided on the outer edge of the lower end 312 aligned with each assembly ramp 352 to provide a visual locator for the lugs 350. The lower end of the mount may be provided with an annular, outwardly extending lip 354 as well, which may serve as a finger stop to discourage placement of the fingers on the protective cover.

An annular spring-receiving recess 360 is disposed in the upper end 310 of the mount 302 between the mount exterior wall 316 and the collar 314. An annular spring-receiving shelf 362 is formed on the interior of a wall of the protective cover 304. The annular shelf opposes the annular spring-receiving recess 360 in the mount. In this manner, the compression spring 308 can be compressed between opposing faces of the shelf 362 and the recess 360, the collar 314 serving to center the spring 308. The spring may comprise any suitable compression spring having a desired spring constant and may be formed of a variety of materials, such as metals or plastics.

During assembly, the spring 308 is inserted into the lower end of the mount 302 such that one end of the spring extends into the annular spring-receiving recess 360 at the upper end of the mount. The other end of the spring is placed against the spring-receiving shelf 362 of the protective cover 304. The cover lugs 350 are aligned visually and/or tactiley with a respective assembly ramp 352, and the upper end 340 of the cover 304 is inserted into the open lower end 312 of the mount 302. As the cover 304 is urged inside the mount 302, the spring 308 is compressed. The lugs 350 of the cover are deflected inwardly as they ride along and finally over the respective ramps 352, as is permitted by their resilient cantilevered construction, to enter the entrance portion 332 of the respective channels 330. The tabs 348 then return to their initial non-deflected positions, thereby causing the lugs 350 to be captured within the respective channel 330 and preventing separation of the cover 304 and the mount 302. The spring 308 is biased solely in compression once the mount and cover are coupled together in the above-described manner.

Having thus assembled the mount 302, cover 304, and spring 308, the needle subassembly 306 is inserted into the mount from the upper end thereof. As noted above, the ribs 326 of the needle subassembly are aligned within the collar 314 of the mount 302 between the stops 324. With the needle subassembly 306 and the mount 302 thus aligned, the subassembly 306 is urged into the mount. The needle protector device 300 is suitable for either manual or automated assembly. When use of the device is desired, the luer fitting 366 of the hub 322 is coupled to a conventional syringe barrel and plunger assembly, such as the illustrative assembly 80 shown in FIG. 7.

The configuration of the channels 330 in the mount 302 permits the protective cover 304 to be in either a locked, needle protection position (shown in FIG. 26) or in one of a plurality of retracted positions to expose the needle during use of the device (shown in FIG. 27) and obviates the need for an armed position and the attendant risks of rotating the device into the armed position. The locked, needle-protection position of the cover 304 corresponds to the lugs 350 of the cover being located in the entrance portion 332 of the respective channel 330 and, more specifically, being located in the detent 356 of the entrance portion 332.

To unlock the device, the lugs 350 must be moved out of the entrance portion 332 by pushing the mount 302 with respect to the cover 304 against the biasing of the compression spring 308 in order to move the lugs out of the respective detent 356 and further, by rotating the cover 304 with respect to the mount 302 past the substantial bend 336 and into the elongated portion 334. The lugs 350 preferably have a rounded corner (best seen in FIGS. 25 and 26) to prevent binding within the bend 336. The channel portion 338 between the entrance portion 332 and the bend 336 is at a predetermined angle which is selected in order to prevent movement of the lug 350 into the elongated portion 334 without a deliberate rotation of the cover 304 with respect to the mount 302. In the illustrative embodiment, the portion 338 is at approximately 18° relative to the lateral axis of the device. With this arrangement, the needle 323 cannot be exposed by merely pushing the mount 302 with respect to the cover 304 against the biasing of the compression spring 308. However, once the lug 350 has been moved past the bend 336 by a rotation, the pushing action is sufficient to retract the cover 304 from the needle 323 as the lugs 350 travel along the respective elongated portions 334 toward the upper end 310 of the mount 302.

In operation of the assembled device 300, it is not necessary to first arm the device, as noted above. Rather, the device is directly actuated by simultaneously pushing the device against a needle-receiving surface 370 and rotating the mount 302 with respect to the cover 304, as best indicated in FIG. 27. Additionally, as noted above, the user can provide this actuation by grasping the barrel and plunger assembly, rather than the mount. The rotation unlocks the device and the pushing action moves the cover 304 further inside the mount 302, with the lugs 350 following the angled path of the elongated portion 334 of the channel 330. In the fully retracted cover position, the lugs are positioned at the far end of the respective channel. Upon withdrawal of the needle and separation of the device from the needle-receiving surface, the compressive force exerted by the spring 308 and the slight torsional bias imparted to the spring during the unlocking cause the cover 304 to be automatically urged back over the needle tip and cause the lugs 350 to return to the entrance portion 332 of the respective channel 330 following the angled path of the slotted channel.

Figure 31:
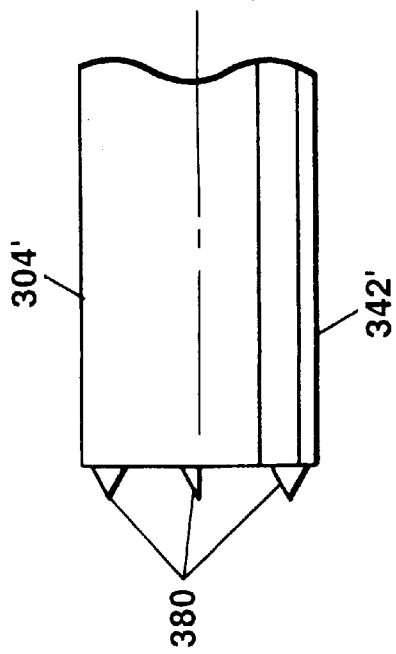
FIG. 31 is a partial side view of the protective cover of the device of FIG. 30.
Figure 30:
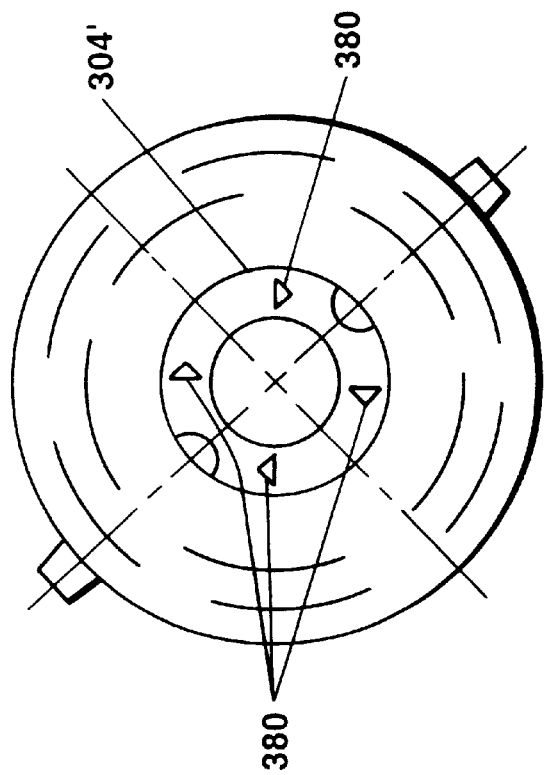
FIG. 30 is an end view of a further embodiment of the needle protector device.

In some applications, a needle must be inserted through a latex plug in an end of a drug vial. Thus, in a further embodiment of the device, illustrated in FIGS. 30 and 31, the protective cover 304' is provided with a plurality of suitably configured sharp points or prongs 380 on the lower end 342'. In use, the prongs bite into the plug in the vial, thereby preventing the device from slipping when the mount is rotated with respect to the cover.

The mount and the protective cover may be comprised of any material having suitable strength and other desired characteristics, such as plastic. Additionally, the mount and cover may be manufactured by any conventional technique, such as injection molding. Preferably, the cover is made from a transparent material so that the tip of the needle is visible in order to facilitate insertion into a needle receiving surface, such as a patient's arm or a vial or ampule. It is further preferable that the mount and cover be comprised of different materials in order to reduce any sticking therebetween over time; for example, the mount may be comprised of the copolymer styrene-acrylonitrile (SAN) from Monsanto of St. Louis, Mo., and the protective cover of a polycarbonate from GE Plastics of Pittsfield, Mass.

The features of the needle protector device 300 of FIGS. 25 through 29 provide safer actuation and permit a simple, effective, and relatively inexpensive manner of assembly. The spring does not require prebiasing in torsion, simplifying both assembly and operation. The device is safer to operate, since it does not require arming by rotating the cover with respect to the mount which requires placing the hand close to the opening through which the needle extends. The device is simpler to operate, in that it needs only to be placed against a needle-receiving surface before actuating the device. The device is safer in that actuation requires simultaneously pushing the device against the needle-receiving surface and turning the mount with respect to the cover, thereby reducing the likelihood of inadvertent actuation. The safety features of the device are further enhanced by the automatic return to the locked position upon removal from the needle-receiving surface.

Referring to FIG. 32, an alternate embodiment of a mount 400 for the needle protector device is shown. The mount 400 is intended for use with a protective cover (like cover 304 of FIG. 25) and a compression spring (like spring 308 of FIG. 25). The mount 304 is substantially cylindrical and has an upper end 404 and an apertured lower end 408. The mount 400 includes two slots, or channels 402 (only one of which can be seen in view of FIG. 32). Like the channel 330 (FIG. 25), channel 402 has an entrance position 406 and an elongated portion 418 which are joined by a substantial bend 428. The slot 402 is adapted for receiving a cantilevered tab 348 of the protective cover 304 (FIG. 25) in the manner described above.

An interior collar 410 of the mount 304 is concentric with an exterior wall 412 and extends from the upper end 404 to terminate at a terminal edge 414. At least a portion of the collar 410 is tapered such that the diameter of the collar at the terminal edge 414 is reduced relative to the diameter of the collar adjacent to the upper end 404. The interior of the collar 410 has at least one thread 416, as shown. In the illustrative embodiment, the thread 416 is a male thread. The needle subassembly 420 may be like the subassembly 120 (FIG. 16) or 306 (FIG. 25) discussed above. To this end, the needle subassembly 420 includes a hub 422 from which a needle 424 extends, as shown. A plurality of ribs 426 project outwardly from the hub 422 and are spaced by slots, or grooves 430. The outer diameter of the needle subassembly 420 as defined by the ribs 426 is slightly larger than at least a portion of the tapered collar 410 adjacent to the collar's terminal edge 414. A conventional Luer fitting 432 is provided at an upper end of the needle hub 422 for coupling to a source of intravenous fluid, such as to a conventional barrel and plunger arrangement.

During manufacture, the needle subassembly 420 is attached to the mount 400 by inserting the hub 422 into the channel defined by the collar 410. The needle subassembly 420 is pushed into the channel of the collar 410 to a predetermined extent. Thereafter, the subassembly 420 is rotated relative to the collar 410. The rotation causes the male screw thread 416 on the interior to the collar 410 to bite into the needle subassembly hub 422. More particularly, the thread 416 carves a slight groove into the ribs 426 of the hub 422. In this way, the needle subassembly 420 is maintained in fixed attachment to the mount 400 and is prevented from being readily removed.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A needle protector device comprising:
   a mount having a needle attachment member for fixedly retaining a needle to the mount and an open end through which the needle can extend;
   a protective cover having an opening through which the needle can extend, the cover being telescopically received within the mount for movement between a locked position in which the cover is disposed over the needle and a retracted position in which the needle is exposed upon simultaneous rotation and translation of the cover with respect to the mount; and
   a resilient member biased in compression between the mount and the cover when the mount is coupled to the cover to urge the cover into the locked position in which the cover is disposed over the needle.

2. The needle protector device of in claim 1, wherein the mount has a channel disposed in a side thereof, the channel including an entrance portion and an elongated portion joined by a bend, and wherein the cover has a lug for engaging the channel of the mount so that, as the cover is moved between the locked position and the retracted position, the lug moves within the channel.

3. The needle protector device of claim 2, wherein the lug is formed on a cantilevered tab formed in a wall of the cover.

4. The needle protector device of claim 2, wherein the cantilevered tab is formed by a U-shaped cut out region in the wall of the cover.

5. The needle protector device of claim 2, wherein the elongated portion extends at an angle with respect to a longitudinal axis of the mount away from the open end of the mount through which the needle can extend.

6. The needle protector device of claim 5, wherein the angle is approximately 30°.

7. The needle protector device of claim 2, wherein the bend is angled sufficiently to prevent movement of the lug out of the entrance portion unless the mount is rotated with respect to the cover.

8. The needle protector device of claim 7, wherein the bend is generally a right angle.

9. The needle protector device of claim 2, wherein the open end of the mount includes a chamfer around its inner circumference to facilitate entry of the lug into the entrance portion during assembly of the needle protector device.

10. The needle protector device of claim 9, wherein the chamfer includes a portion having a different angle located adjacent to the entrance portion of the channel to provide an assembly ramp, the different angle providing a tactile locator for aligning the lug with the entrance portion.

11. The needle protector device of claim 9, wherein the mount includes a visual locator member disposed on the exterior of the mount adjacent the entrance portion.

12. The needle protector device of claim 11, wherein the visual locator member comprises a detent.

13. The needle protector device of claim 1, wherein the needle attachment member is formed at an opposite end of the mount from the open end through which the needle can extend.

14. The needle protector device of in claim 1, wherein the needle attachment member is sized to frictionally engage and retain a needle subassembly, including a needle, sufficiently to prevent removal of the needle subassembly.

15. The needle protector device of claim 14, wherein the needle attachment member includes a rotational stop member to prevent rotation of the needle subassembly relative to the mount, whereby rotation of the mount with respect to the cover can be effectuated by rotation of the needle subassembly.

16. The needle protector device of claim 15, wherein the rotational stop member comprises a radially inwardly facing protrusion located to engage between a pair of ribs formed on the needle subassembly.

17. The needle protector device of claim 1, wherein the needle attachment member comprises a male thread disposed on an interior channel of the mount into which the needle subassembly is rotated.

18. The needle protector device of claim 1, wherein the resilient compression member comprises a compression spring.

19. The needle protector device of claim 18, wherein a first end of the compression spring is received against a spring-receiving surface in the mount and a second end of the spring is received against a spring-receiving surface in the cover, the respective spring-receiving surfaces being in opposition to each other.

20. The needle protector device of claim 19, wherein the spring-receiving surface in the cover comprises a shelf formed in an interior wall of the cover.

21. The needle protector device of claim 19, wherein the spring-receiving surface in the mount comprises an interior end wall of the mount opposite the open end of the mount.

22. The needle protector device of claim 19, wherein the needle attachment member of the mount comprises a collar member extending concentrically inwardly, the compression member comprising a spring received over the collar member.

23. The needle protector device of claim 1, wherein the mount includes an outwardly extending annular lip around the open end.

24. The needle protector device of claim 1, wherein the cover includes at least one prong disposed adjacent the opening through which the needle can extend, the prong configured to bite into a needle-receiving surface, whereby the device is prevented from slipping during rotation of the cover with respect to the mount.

25. A needle protector device comprising:
 a mount having a first end at which a needle attachment member is disposed for fixedly retaining a needle to the mount and a second, open end through which the needle can extend;
 a protective cover having an opening through which the needle can extend, the cover coupled to the mount for movement between a locked position in which the cover is disposed over the needle and a retracted position in which the needle is exposed upon simultaneous rotation and translation of the cover with respect to the mount; and
 a resilient member biased in compression between the mount and the cover when the mount is coupled to the cover to urge the cover into the locked position in which the cover is disposed over the needle.

* * * * *

UNITED STATES PATENT AND TRADEMARK OFFICE
CERTIFICATE OF CORRECTION

PATENT NO.   : 5,984,899                                 Page 1 of 1
DATED        : November 16, 1999
INVENTOR(S)  : D'Alessio et al.

It is certified that error appears in the above-identified patent and that said Letters Patent is hereby corrected as shown below:

Column 3,
Line 52, reads "biassing" and should read -- biasing --.

Column 5,
Line 37, reads "and isometric" and should read -- an isometric --.

Column 6,
Line 28, reads "3 3" and should read -- 3-3 --.

Column 9,
Line 29, reads "Each of apertures" and should read -- Each of the apertures --.

Column 16,
Line 46, reads "fly" and should read -- firmly --.

Column 20,
Line 50, reads "of in claim 1" and should read -- of claim 1 --.

Signed and Sealed this

Twenty-first Day of May, 2002

*Attest:*

*Attesting Officer*

JAMES E. ROGAN
*Director of the United States Patent and Trademark Office*